(12) United States Patent
Petkovich et al.

(10) Patent No.: US 8,592,401 B2
(45) Date of Patent: Nov. 26, 2013

(54) METHODS AND COMPOUNDS FOR VITAMIN D THERAPY

(75) Inventors: P. Martin Petkovich, Kingston (CA); Charles W. Bishop, Mount Horeb, WI (US); Eric J. Messner, Lake Forest, IL (US); Keith H. Crawford, Denver, CO (US)

(73) Assignees: Proventiv Therapeutics, LLC, Bannockburn, IL (US); Cytochroma Inc., Markham, Ontario (CA)

( * ) Notice: Subject to any disclaimer, the term of this patent is extended or adjusted under 35 U.S.C. 154(b) by 413 days.

(21) Appl. No.: 12/597,224

(22) PCT Filed: Apr. 25, 2008

(86) PCT No.: PCT/US2008/061586
§ 371 (c)(1),
(2), (4) Date: Apr. 16, 2010

(87) PCT Pub. No.: WO2008/134518
PCT Pub. Date: Nov. 6, 2008

(65) Prior Publication Data
US 2010/0204189 A1    Aug. 12, 2010

Related U.S. Application Data

(60) Provisional application No. 60/913,848, filed on Apr. 25, 2007.

(51) Int. Cl.
*A61K 31/59*    (2006.01)
(52) U.S. Cl.
USPC .................................................. 514/167

(58) Field of Classification Search
USPC ........................................................ 514/167
See application file for complete search history.

(56) References Cited

U.S. PATENT DOCUMENTS

| | | | |
|---|---|---|---|
| 3,565,924 A | 2/1971 | DeLuca et al. | |
| 3,880,894 A | 4/1975 | De Luca et al. | |
| 4,004,003 A | 1/1977 | Babcock et al. | |
| 4,230,701 A | 10/1980 | Holick et al. | |
| 4,335,120 A | 6/1982 | Holick et al. | |
| 4,508,651 A * | 4/1985 | Baggiolini et al. | ........... 552/653 |
| 4,555,364 A | 11/1985 | DeLuca et al. | |
| 4,668,517 A | 5/1987 | Weber et al. | |
| 4,684,524 A | 8/1987 | Eckenhoff et al. | |

(Continued)

FOREIGN PATENT DOCUMENTS

| | | |
|---|---|---|
| CA | 2241205 A1 | 7/1997 |
| EP | 0227836 A1 | 7/1987 |

(Continued)

OTHER PUBLICATIONS

Jones et al., Biochemistry, 1975:14(6):1250-1256.*

(Continued)

*Primary Examiner* — San-Ming Hui
(74) *Attorney, Agent, or Firm* — Marshall, Gerstein & Borun LLP

(57) ABSTRACT

Methods and compositions comprising 1,25-dihydroxyvitamin $D_2$ are disclosed. A method for lowering or maintaining lowered serum parathyroid hormone in human patients including administering to said patients an effective amount of 1,25-dihydroxyvitamin $D_2$ to lower or maintain lowered serum parathyroid hormone levels is disclosed. Dosage forms and dosing regimens are also disclosed.

21 Claims, 6 Drawing Sheets

* - p<0.02 compared to adenine diet vehicle
** - p<0.0003 compared to normal diet vehicle

(56) References Cited

U.S. PATENT DOCUMENTS

| | | | |
|---|---|---|---|
| 4,695,591 | A | 9/1987 | Hanna et al. |
| 4,721,613 | A | 1/1988 | Urquhart et al. |
| 4,729,895 | A | 3/1988 | Makino et al. |
| 4,755,544 | A | 7/1988 | Makino et al. |
| 5,026,559 | A | 6/1991 | Eichel et al. |
| 5,160,742 | A | 11/1992 | Mazer et al. |
| 5,328,903 | A | 7/1994 | Ishii et al. |
| 5,403,831 | A | 4/1995 | DeLuca et al. |
| 5,487,900 | A | 1/1996 | Itoh et al. |
| 5,529,991 | A | 6/1996 | Knutson et al. |
| 5,593,690 | A | 1/1997 | Akiyama et al. |
| 5,602,116 | A | 2/1997 | Knutson et al. |
| 5,614,513 | A | 3/1997 | Knutson et al. |
| 5,622,941 | A | 4/1997 | Knutson et al. |
| 5,693,615 | A | 12/1997 | Stone |
| 5,707,980 | A | 1/1998 | Knutson et al. |
| 5,795,882 | A | 8/1998 | Bishop et al. |
| 5,861,386 | A | 1/1999 | Knutson et al. |
| 5,869,473 | A | 2/1999 | Knutson et al. |
| 6,051,567 | A | 4/2000 | Abrahamson et al. |
| 6,133,250 | A | 10/2000 | Knutson et al. |
| 6,139,875 | A | 10/2000 | Adams et al. |
| 6,147,064 | A | 11/2000 | Knutson et al. |
| 6,150,346 | A | 11/2000 | Knutson et al. |
| 6,190,591 | B1 | 2/2001 | van Lengerich |
| 6,190,695 | B1 | 2/2001 | Hoshino et al. |
| 6,228,849 | B1 | 5/2001 | Thys-Jacobs |
| 6,265,392 | B1 | 7/2001 | Abrahamson et al. |
| 6,274,169 | B1 | 8/2001 | Abrahamson et al. |
| 6,342,249 | B1 | 1/2002 | Wong et al. |
| 6,376,479 | B1 | 4/2002 | Knutson et al. |
| 6,380,408 | B1 | 4/2002 | Posner et al. |
| 6,432,936 | B1 | 8/2002 | DeLuca et al. |
| 6,596,314 | B2 | 7/2003 | Wong et al. |
| 6,903,083 | B2 | 6/2005 | Knutson et al. |
| 6,923,988 | B2 | 8/2005 | Patel et al. |
| 6,929,803 | B2 | 8/2005 | Wong et al. |
| 6,982,258 | B2 | 1/2006 | Posner et al. |
| 7,101,865 | B2 | 9/2006 | Posner et al. |
| 2002/0183288 | A1 | 12/2002 | Mazess et al. |
| 2004/0043971 | A1 | 3/2004 | Mazess et al. |
| 2004/0101554 | A1 | 5/2004 | Kirschner et al. |
| 2005/0101576 | A1 | 5/2005 | Whitehouse et al. |
| 2005/0124591 | A1 | 6/2005 | Tian et al. |
| 2005/0148557 | A1 | 7/2005 | Tian et al. |
| 2006/0193877 | A1 | 8/2006 | Tengler et al. |
| 2009/0176748 | A1 | 7/2009 | Tabash et al. |
| 2009/0311316 | A1 | 12/2009 | Bishop et al. |

FOREIGN PATENT DOCUMENTS

| | | |
|---|---|---|
| EP | 0508756 A1 | 10/1992 |
| JP | 04-208225 A | 7/1992 |
| JP | 7242550 A | 9/1995 |
| JP | 8-92098 A | 4/1996 |
| JP | 10-158171 A | 6/1998 |
| JP | 2004175750 A | 6/2004 |
| WO | WO-91/12807 A1 | 9/1991 |
| WO | WO-91/16899 A1 | 11/1991 |
| WO | WO-94/00128 A1 | 1/1994 |
| WO | WO-96/00074 A1 | 1/1996 |
| WO | WO-96/31215 A1 | 10/1996 |
| WO | WO-97/11053 A1 | 3/1997 |
| WO | WO-98/18610 A1 | 5/1998 |
| WO | WO-99/11272 A1 | 3/1999 |
| WO | WO-00/21504 A1 | 4/2000 |
| WO | WO-00/35419 A2 | 6/2000 |
| WO | WO-03/039521 A1 | 5/2003 |
| WO | WO-03/039572 A1 | 5/2003 |
| WO | WO-03/047595 A1 | 6/2003 |
| WO | WO-2004/028515 A1 | 4/2004 |
| WO | WO-2004/058235 A2 | 7/2004 |
| WO | WO-2005/011652 A2 | 2/2005 |
| WO | WO-2005/123120 A1 | 12/2005 |
| WO | WO-2007/047327 A2 | 4/2007 |
| WO | WO-2008/008608 A2 | 1/2008 |
| WO | WO-2008/134523 A1 | 11/2008 |
| WO | WO-2010/011906 A1 | 1/2010 |

OTHER PUBLICATIONS

Lips, *Endocrine Reviews*, 2001;22:477-501.*

Gonzalez et al., *Am J. Nephrol.*, 2004;24:503-510.*

"K/DOQI Clinical Practice Guidelines for Bone Metabolism and Disease in Chronic Kidney Disease," National Kidney Foundation, *Am. J. Kidney Dis.*, 42 (Supplement 3):1-202 (2003).

Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).

Andress, "Vitamin D in chronic kidney disease: A systematic role for selective vitamin D receptor activation," *Kidney Int.*, 69:33-43 (2006).

Arekat et al., "Dramatic Improvement of BMD Following Vitamin D Therapy in a Bone Marrow Transplant Recipient," *J. Clin. Densitometry*, 5:267-271 (2002).

Armas et al., "Vitamin $D_2$ is Much Less Effective than Vitamin $D_3$ in Humans," *J. Clin. Endocrinol. Metab.*, 89:5387-5391 (2004).

Bagnis et al., "Biochemical and Hormonal Short-Term Effects of 25-hydroxyvitamin D3 in Patients on Continuous Peritoneal Dialysis," *Ital. J. Mineral Electrolyte Metab.*, 12:73-76 (1998).

Bailie et al. "Comparative Review of the Pharmacokinetics of Vitamin D Analogues," *Seminars in Dialysis*, 15(5):352-357 (2000).

Baird et al., "Steroid Dynamics Under Steady-State Conditions," *Recent Prog. Horm. Res.*, 25:611-664 (1969).

Barger-Lux M.J. et al., "Vitamin D and Its Major Metabolites: Serum Levels After Graded Oral Dosing in Healthy Men" *Osteoporosis International*, United Kingdom, 8(3):222-230 (1998).

Beckman, et al., "Up-Regulation of the Intestinal 1, 25-Dihydroxyvitamin D Receptor During Hypervitaminosis D: A Comparison Between Vitamin D2 and Vitamin D31," *Biochemical and Biophysical Research Communications*, 169(3):910-915 (1990).

Beer et al., "Pharmacokinetics and Tolerability of a Single Dose of DN-101, a New Formulation of Calcitriol, in Patients with Cancer," *Clin. Cancer Res.*, 11:7794-7799 (2005).

Bell et al., "Evidence that 1,25-Dihydroxyvitamin D3 Inhibits the Hepatic Production of 25-Hydroxyvitamin D in Man," *J. Clin. Invest.*, 74:1540-1544 (1984).

Bianchi et al., "No Difference in Intestinal Strontium Absorption After an Oral or an Intravenous 1,25($OH)_2D_3$ Bolus in Normal Subjects," *J. Bone Miner. Res.*, 14:1789-1795 (1999).

Brossard et al. "Influence of Glomerular Filtration Rate on Non-(1-84) Parathyroid Hormone (PTH) Detected by Intact PTH Assays," *Clinical Chemistry*, 46(5):697-703 (2000).

Budavari (ed.), *Merck Index: an Encyclopedia of Chemicals, Drugs, and Biologicals*, 11th Edition, Merck & Co., 9927-9930 (1989).

Claris-Appiani et al., "Phosphate-Induced PTH Stimulation and Calcitriol Treatment in Children with Early Chronic Renal Insufficiency," *J. Bone Miner. Met.*, 12:S91-S97 (1994).

Coburn, "An Update on Vitamin D as Related to Nephrology Practice: 2003," *Kidney International*, 64(87):S125-S130 (2003).

Coburn, et al., "Use of Active Vitamin D Sterols in Patients with Chronic Kidney Disease, Stages 3 and 5," *Kidney International*, 63(85):S49-S53 (2003).

Coen et al., "1,25($OH)_2D_3$ and 25-$OHD_3$ in the Treatment of Renal Osteodystrophy: Comparison of Combined Versus 1,25($OH)_2D_3$ Administration Alone," *Miner. Electrolyte Metab.*, 9:19-27 (1983).

Cohen-Solal et al., "Non-Aluminic Adynamic Bone Disease in Non-Dialyzed Uremic Patients: A New Type of Osteopathy Due to Overtreatment?" *Bone*, 13:1-5 (1992).

Collet et al. "Modified-Release Peroral Dosage Forms," Aulton (ed.), Pharmaceutics: The Science of Dosage Forms, Churchill Livingston, London, pp. 289-305 (2002).

Cooke et al., "Vitamin D-Binding Protein (Gc-Globulin): Update 1995," *Endocrine Rev.*, 4:125-128 (1995).

Daisley-Kydd et al., "Calcitriol in the Management of Secondary Hyperparathyroidism of Renal Failure," *Pharmacotherapy.*, 16:619-630 (1996).

(56) References Cited

OTHER PUBLICATIONS

Davies, et al. The Absorption and Metabolism of Vitamin D3 from Parenteral Injection Sites, Proceedings of the Workshop on Vitamin D, 4th, Vitam. D: Basic Res. Its Clin. Appl. pp. 610-612 (1979).
Deroisy et al., "Comparison of the Short-Term Effects of Three Oral Calcium-Vitamin D Formulations and Placebo on Calcium Metabolism," *Curr. Ther. Res.*, 59:370-378 (1998).
Deville et al., "Effect of Ergocalciferol Supplementation on Serum Parathyroid Hormone and Serum 25-Hydroxyvitamin D in Chronic Kidney Disease," *Nephrology*, 11:555-559 (2006).
*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).
*Dietary Supplement Fact Sheet: Vitamin D*, National Institutes of Health, Office of Dietary Supplements (last update: Aug. 5, 2005), retrieved from <URL: http:ods.od.nih.gov/factsheets/vitamind.asp> on Aug. 31, 2007.
*Disease and Vitamin D*, University of California Riverside, retrieved from Internet, <URL: <http://vitamind.ucr.edu/disease.html>> (last update: May 19, 1999).
Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30, 2007.
Dusso et al, "Metabolic Clearance Rate and Production Rate of Calcitriol in Uremia," *Kidney International*, 35 860-864 (1989).
Dusso et al., "Extrarenal Production of Calcitrol in Normal and Uremic Humans*," *Journal of Clinical Endocrinology and Metabolism* 72(1):157-164 (1991).
Eastwood et al., "The Effect of 25-Hydroxy Vitamin $D_3$ in the Osteomalacia of Chronic Renal Failure," *Clin. Sci. Molec. Med.*, 52:499-508 (1977).
Fernandez et al., "Guidelines for Dosing of Intravenous Calcitriol in Dialysis Patients with Hyperparathyroidism," *Nephrol. Dial. Transplant.*, 11:96-101 (1996).
Fournier et al., "1-alpha-Hydroxycholecalciferol and 25-Hydroxycholecalciferol in Renal Bone Disease," *Calcified Tissues 1975: Proceedings of the 11th European Symposium on Calcified Tissues*, 226-235 (1976).
Fournier et al., "Advances in Nephrology from the Necker Hospital" *Adv. Nephrol Necker Hosp.* 21:237-306 (1992).
Fournier et al., "Comparison of 1α-hydroxycholecalciferol and 25-hydroxycholecalciferol in the treatment of renal osteodystrophy: Greater effect of 25-hydroxycholecalciferol on bone mineralization" *Kidney International* 15:196-204 (1979).
Fournier et al., "Current Status of the Management of Renal Osteodystrophy" *Proceedings of the European Dialysis and Transplant Association* 15:547-568 (1978).
Fournier et al., "Low doses of calcitriol or calcium carbonate for the prevention of hyperparathyroidism in predialysis patients?" *Nephrol Dial Transplant* 11(7):1493-1495 (1996).
Fournier et al., "Present-Day Concepts in the Treatment of Chronic Renal Failure" *Contrib Nephrol*. 71:64-80 (1989).
Fournier et al., "Preventing Renal Bone Disease in Moderate Renal Failure with $CaCO_3$ and 25(OH) Vitamin $D_3$," *Kidney Int.*, 33:S178-S279 (1988).
Fournier et al., "Renal Osteodystrophy in Dialysis Patients: Diagnosis and Treatment," *Artificial Organs*, 22:530-557 (1998).
Fournier et al., "Renal Osteodystrophy: Pathophysiology and Treatment" *Hormone Res.* 20:44-58 (1984).
Fournier et al., "The Approach to the Treatment of Secondary Hyperparathyroidism in Early Renal Failure" *Am. J. Nephrol* 8:170-172 (1988).
Fournier et al., "Traitement vitaminique D et ostéodystrophies rénales: indications et modalitiés" *Nephrologie* 16(2):165-190 (1995) [journal in French].
Fournier et al., 1α Hydroxycholecalciferol and 25 Hydroxycholecalciferol in Renal Bone Disease *Proc Eur Dial Transplant Assoc* 12:227-236 (1976).

Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).
Friedman et al. "The Role of Vitamin D in Mild to Moderate Chronic Kidney Disease," *Trends in Endocrinology & Metab,.* 13(5):189-194 (2002).
Gallagher et al., "Comparison of the Histological Effect and Metabolism of 25-(OH)D and 1,25-(OH)2D in Rat Bone," p. 399-401, In: Norman, *Vitamin D: Basic Research and its Clinical Application: Proceedings of the Fourth Workshop on Vitamin D*, Berlin, West Germany, Feb. 1979.
Ghazali et al., "Is low plasma 25-(OH) vitamin D a major risk factor for hyperparathyroidism and Looser's zones independent of calcitriol?" *Kidney International* 55:2169-2177 (1999).
Haddad et al., "Acute Administration of 25-Hydroxycholecalciferol in Man," *J. Clin. Endocrinol. Metab.*, 42:284-289 (1976).
Haddad et al., "Human Serum Binding Capacity and Affinity for 25-Hydroxyergocalciferol and 25-Hydroxycholecalciferol," *J. Clin. Endocrinol. Metab.*, 43:86-91 (1976).
Haddad et al., "Natural and Synthetic Sources of Circulating 25-Hydroxyvitamin D in Man," *Nature*, 244:515-517 (1973).
Haddad, "Plasma Vitamin D-binding Protein (Gc-Globulin): Multiple Tasks," *J. Steroid Biochem. Molec. Biol.*, 53:579-582 (1995).
Haddad, "Seasonal Diminution of Vitamin D Stores in the United States: Can Darker Winters Lead to Lighter Bones?" *Trends Endocrinol. Metab.*, 7:209-212 (1996).
Haddad, "Traffic, Binding and Cellular Access of Vitamin D Sterols," *Bone and Mineral Res.*, Elsevier, 5:281-308 (1987).
Haddad, "Vitamin D—Solar Rays, The Milky Way, or Both?" *NEJM*, 326:1213-1215 (1992).
Halloran et al., "Plasma Vitamin D Metabolite Concentrations in Chronic Renal Failure: Effect of Oral Administration of 25-Hydroxyvitamin D3," *J. Clin. Endocrin. & Metab.*, 59:1063-1069 (1984).
Hamida et al., "Hyperparathyroïdie secondaire ál"insuffisance rénale" *Annales d'Endocrinologie* 55:147-158 (1994) [reference in French].
Hannula et al., "Constant, But Not Pulsed Calcitriol Suppresses Hemodialysis Patients' Antigen-Induced Lymphocyte Proliferation," *Nephron*, 86:139-144 (2000).
Hay et al., "Vitamin D2 in Vertebrate Evolution," *Comp. Biochem. Physiol. B*, 56:375-380 (1977).
Holick, "Vitamin D Deficiency in CKD: Why Should We Care?" *Am. J. Kidney Dis.*, 45:1119-1121 (2005).
Horst et al., "A Sensitive Competitive Protein Binding Assay for Vitamin D in Plasma," *Steroids*, 37:581-592 (1981).
Horst et al., "Discrimination in the Metabolism of Orally Dosed Ergocalciferol and Cholecalciferol by the Pig, Rat and Chick," *Biochem. J.*, 204:185-189 (1982).
Horst et al., "Rat cytochrome P450C24 (CYP24) does not metabolize 1,25-dihydroxyvitamin $D_2$ to calcitroic acid," *J. Cell Biochem.*, 88:282-285 (2003).
Hottelart et al., "Ostéodystrophie rénale (2): son traitement chez l'insuffisant rénal avant la dialyse" *Nephrologie* 21(6):275-282 (2000) [reference in French].
Houghton et al., "The Case Against Ergocalciferol (Vitamin $D_2$) as a Vitamin Supplement," *Am. J. Clin. Nutr.*, 84:694-697 (2006).
Hunt, et al., "A Comparison of the Toxicity of Ergocalciferol and Cholecalciferol in Rhesus Monkeys (*Macaca mulatta*)," *J. Nutrition*, 102:975-986 (1972).
Hussar, "New Drugs of 1999," *J. Am. Pharmacist. Assoc.* 40(2)1 81-229 (2000).
Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," *Kidney Int.*, 55:1019-1027 (1999).
Jara et al., "Effect of Calcitriol Treatment and Withdrawal on Hyperparathyroidism in Haemodialysis Patients with Hypocalcaemia," *Nephroi. Dial. Transplant.*, 16:1009-1016 (2001).

(56) References Cited

OTHER PUBLICATIONS

Jean et al., "Daily Oral 25-Hydroxycholecalciferol Supplementation for Vitamin D Deficiency in Haemodialysis Patients: Effects on Mineral Metabolism and Bone Markers," *Nephrol. Dial. Transplant*, 23:3670-3676 (2008).

Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" *Nephron. Clin. Pract.* 110:c58-c65 (2008).

Jean et al., "Monthly cholecalciferol administration in heamodialysis patients: a simple and efficient strategy for vitamin D supplementation" *Nephrol. Dial. Transplant* 24(12):3799-3805 (2009).

Kajihara et al., "Novel Method to Control Release of Lipophilic Drugs with High Potency from Silicone," *Chem. Pharm. Bull.*, 51:11-14 (2003).

Kalantar-Zadeh et al., "Clinical Outcomes with Active versus Nutritional Vitamin D Compounds in Chronic Kidney Disease" *Clin J Am Soc Nephrol.* 4(9):1529-1539 (2009).

Kanis et al., "Rate of Reversal of Hypercalcaemia and Hypercalciuria Induced by Vitamin D and Its 1-alpha-Hydroxylated Derivatives," *BMJ*, 1:78-81 (1977).

Kim, *Advanced Pharmaceutics: Physicochemical Principles*, pp. 362-392, Boca Raton, Fla: CRC Press (2004).

Koshikawa, et al., "Clinical Effect of Intravenous Calcitriol Administration on Secondary Hyperparathyroidism," *Nephron*; 90:413-423 (2002).

Laclair et al., "Prevalence of Calcidiol Deficiency in CKD: A Cross-Sectional Study Across Latitudes in the United States," *Am. J. Kidney Dis.*, 45:1026-1033 (2005).

Lafage et al., "Ketodiet, Physiological Calcium Intake and Native Vitamin D Improve Renal Osteodystrophy," *Kidney Int.*, 42:1217-1225 (1992).

Lambert et al., "Evidence for Extranrenal Production of 1-alpha,25-Dihydroxyvitamin D in Man," *J. Clin. Invest.*, 69:722-725 (1982).

Lambrey et al., "24, 25 Dihydroxycalciferol: Assay in Non-Anephric Patients on Chronic Haemodialysis and Assessment of it's Possible Pathophysiological Role in Renal Osteodystrophy" *Proc Eur Dial Transplant Assoc.* 17:548-556 (1980).

Lambrey, "Possible Link Between Changes in Plasma 24,25-Dihydroxyvitamin D and Healing of Bone Resorption in Dialysis Osteodrstrophy" *Metab. Bone Dis. & Rel. Res.* 4:25-30 (1982).

Langman et al., "25-Hydroxyvitamin D3 (Calcifediol) Therapy of Juvenile Renal Osteodystrophy: Beneficial Effect on Linear Growth Velocity," *J. Pediatrics*, 100:815-820 (1982).

Larrosa M. et al., Long-Term Treatment of Hypovitaminosis D. Calcidol or Cholecalciferol? *Annals of the Rheumatic Diseases*, vol. 64, No. Suppl. 3, Jul. 2005, p. 366.

Lau et al., "Vitamin D Therapy of Osteoporosis: Plain Vitamin D Therapy Versus Active Vitamin D Analog (D-Hormone) Therapy," *Calcif. Tissue Int.*, 65:295-306 (1999).

Lehmann et al., "Coating of Tablets and Small Particles with Acrylic Resins by Fluid Bed Technology," *Int. J. Pharm. Tech. & Prod. Mfr.*, 2:31-43 (1981).

Letteri et al., "Effects of 25-Hydroxycholecalciferol on Calcium Metabolism in Chronic Renal Failure" *Adv. Exp. Med. Biol.* 81:591-601 (1977).

Lomonte et al., "Are Low Plasma Levels of 25-(OH) Vitamin D a Major Risk Factor for Hyperparathyroidism Independent of Calcitriol in Renal Transplant Patients?" *J. Nephrol.*, 18:96-101 (2005).

Maierhofer et al., "Synthesis and Metabolic Clearance of 1,25-Dihydroxyvitamin D as Determinants of Serum Concentrations: a Comparison of Two Methods" *Journal of Clinical Endocrinology and Metabolism* 53:472-475 (1981).

Manni et al., "Oral Calcitriol: Comparison Between the Same Weekly Dose Administered as a Single vs. Two Divided Pulsed Doses in Secondary Hyperparathyroidism of Chronic Renal Failure," *Ital. J Mineral Electrolyte Metab.*, 11:61-64 (1997).

Mazouz et al., "Risk factors of renal failure progression two years prior to dialysisis" *Clinical Nephrology* 51(6):355-366 (1999).

Messa et al., "Direct In Vivo Assessment of Parathyroid Hormone-Calcium Relationship Curve in Renal Patients," *Kidney Int.*, 46:1713-1720 (1994).

Moe et al., "Safety and Efficacy of Pulse and Daily Calcitriol in Patients on CAPD: A Randomized Trial," *Nephrol. Dial. Transplant.*, 13:1234-1241 (1998).

Morris, "Vitamin D: A Hormone for All Seasons—How Much is Enough?" *Clin. Biochem. Rev.*, 26:21-32 (2005).

Muindi et al., "Phamacokinetics of Liquid Calcitriol Formulation in Advanced Solid Tumor Patients: Comparison with Caplet Formulation," *Cancer Chemother. Pharmacol.*, 56:492-496 (2005).

Nakanishi et al., "Clinical Role of Vitamin D viewed from the new viewpoint. The Roles of Vitamin D in Secondary Hyperparathyroidism," *Clinical Endocrinology* (Tokyo) [journal in Japanese] 52(11):1107-1112 (2004).

Parfitt et al., "Calcitrol But No Other Metabolite of Vitamin D is Essential for NormalBone Growth and Development in the Rat," *J. Clin. Invest.*, 73:576-586 (1984).

Peacock et al., "Effect of Calcium or 25OH Vitamin D3 Dietary Supplementation on Bone Loss at the Hip in Men and Women over the Age of 60" *The Journal of Clinical Endocrinology & Metabolism*, 85(9):3011-3019 (2007).

Phadnis et al., "Direct, Rapid Effects of 25-Hydroxyvitamin D3 on Isolated Intestinal Cells," *J. Cell. Biochem.*, 90:287-293 (2003).

Pourgholami et al., "1, 25-Dihydroxyvitamin $D_3$ Dissolved in Lipiodol Produces a Sustained Antiproliferative Effect in the Human Hepatoblastoma Cell Line HepG2," *Anticancer Res.*, 20:723-728 (2000).

Pourgholami et al., "In Vitro Antiproliferative Activity of a Medium-Chain Triglyceride Solution of 1, 25-Dihydroxyvitamin $D_3$ in HepG2 Cells," *Anticancer Res.*, 20:4257-4260 (2000).

Rapuri, P.B. et al., "Effect of Vitamins D2 and D3 Supplement Use on Serum 25-OHD Concentration in Elderly Women in Summer and Winter," *Calcified Tissue International*, 74(2):150-156 (2004).

Reddy et al., *Abstracts Sixth Annual Scientific Meeting of the American Society for Bone and Mineral Research*, 36:524 (1984).

Reichel et al., "Calcium Metabolism in Early Chronic Renal Failure: Implications for the Pathogenesis of Hyperparathyroidism," *Nephrol. Dial. Transplant.*, 6:162-169 (1991).

Reichel et al., "Intermittent Versus Continuous Administration of 1,25-dihydroxyvitamin $D_3$ in experimental renal hyperparathyroidism," *Kidney Int.*, 44:1259-1265 (1993).

Reichel, "Current treatment options in secondary renal hyperparathyroidism," *Nephrol Dial Transplant* 21:23-28 (2006).

Ritter et al., "25-Hydroxyvitamin $D_3$ suppresses PTH synthesis and secretion by bovine parathyroid cells," *Kidney Int.*, 70:654-659 (2006).

Saab et al., "Prevalence of Vitamin D Deficiency and the Safety and Effectiveness of Monthly Ergocalciferol in Hemodialysis Patients," *Nephron Clin. Pract.*, 105:c132-c138 (2007).

Sanchez, "Prevention and Treatment of Renal Osteodystrophy in Children With Chronic Renal Insufficiency and End-Stage Renal Disease," *Seminars in Nephrology*, 21:441-450 (2001).

Sebert et al., "Effets a Long Terme D'Une Association De 25-Hydroxycholécalciférol et de 1-Alpha-Hydroxycholécalciférol Sur L'Ostéodystrophie Des Hémodialysés Chroniques" *Rev. Rhum Mal Osteoartic* 48(7-9):535-541 (1981).

Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," *Metab. Bone Dis. & Rel. Res.*, 2:217-222 (1980).

Sebert et al. "Comparative effects of equal doses of vitamin D2 and vitamin D3 for the correction of vitamin D deficiency in the elderly" in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).

Sekkarie, "The Impact of Over-the-counter Vitamin D Supplementals on Vitamin D and Parathyroid Hormone Levels in Chronic Kidney Disease," *Clin. Nephrology*, 65:91-96 (2006).

(56) References Cited

OTHER PUBLICATIONS

Sjoden, et al., "1α-Hydroxyvitamin $D_2$ is Less Toxic than 1α-Hydroxyvitamin $D_3$ in the Rat," *Society for Experimental Biology and Medicine*, 179: 432-436 (1985).

Somerville et al., "Resistance to Parathyroid Hormone in Renal Failure: Role of Vitamin D Metabolites," *Kidney Int.*, 14:245-254 (1978).

Sommerfeldt et al., "Metabolism of Orally Administered [$^3$H]Ergocalciferol and [$^3$H]Cholecalciferol by Dairy Calves," *J. Nutr.*, 113:2595-2600 (1983).

Stamp et al., "Comparison of Oral 25-Hydroxycholecalciferol, Vitamin D, and Ultraviolet Light as Determinants of Circulating 25-Hydroxyvitamin D," *The Lancet*, 309:1341-1343 (1977).

Stein et al., "An Update on the Therapeutic Potential of Vitamin D Analogues," *Expert Opin. Investig. Drugs*, 12:825-840 (2003).

Stumpf, "The Dose Makes the Medicine," *Drug Discovery Today*, 11:550-555 (2006).

Szycher, *Szycher's Dictionary of Biomaterials and Medical Devices*, pp. 20, 48, 127, Lancaster, Penn: Technomic Publishing Co., Inc. (1992).

Sömjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," *Steroids*, 63:340-343 (1998).

Taylor et al., "Interrelationship of Serum 25-Hydroxyvitamin $D_2$ and 1,25-Dihydroxyvitamin D in Juvenile Renal Osteodystrophy after Therapy with 25-Hydroxyvitamin $D_3$," *Metab. Bone Dis. & Rel. Res.*, 4:255-261 (1982).

Teitelbaum et al., "Calcifediol in Chronic Renal Insufficiency" *JAMA* 235(2):164-167 (1976).

Thomas et al., "Hypovitaminosis D in Medical Inpatients," *NEJM*, 338:777-783 (1998).

Van Weelden et al., "Apoptotic Regression of MCF-7 Xenografts in Nude Mice Treated with the Vitamin $D_3$ Analog, EB1089," *Endocrinology*, 139:2102-2110 (1998).

Vieth, "What is the optimal vitamin D status for health?" *Prog. Biophys. Mol. Biol.*, 92:26-32 (2006).

Wise (ed.), *Handbook of Pharmaceutical Controlled Release Technology*, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).

Witmer et al., "Effects of 25-hydroxycholecalciferol on bone lesions of children with terminal renal failure" *Kidney International* 10:395-408 (1976).

Zerwekh et al., "Extra-Renal Production of 24,25-Dihydroxyvitamin D in Chronic Renal Failure During 25 Hydroxyvitamin $D_3$ Therapy," *Kidney Int.*, 23:401-406 (1983).

Zisman et al., "Impact of Ergocalciferol Treatment of Vitamin D Deficiency on Serum Parathyroid Hormone Concentrations in Chronic Kidney Disease," *Am. J. Nephrol.*, 27:36-43 (2007).

\* cited by examiner

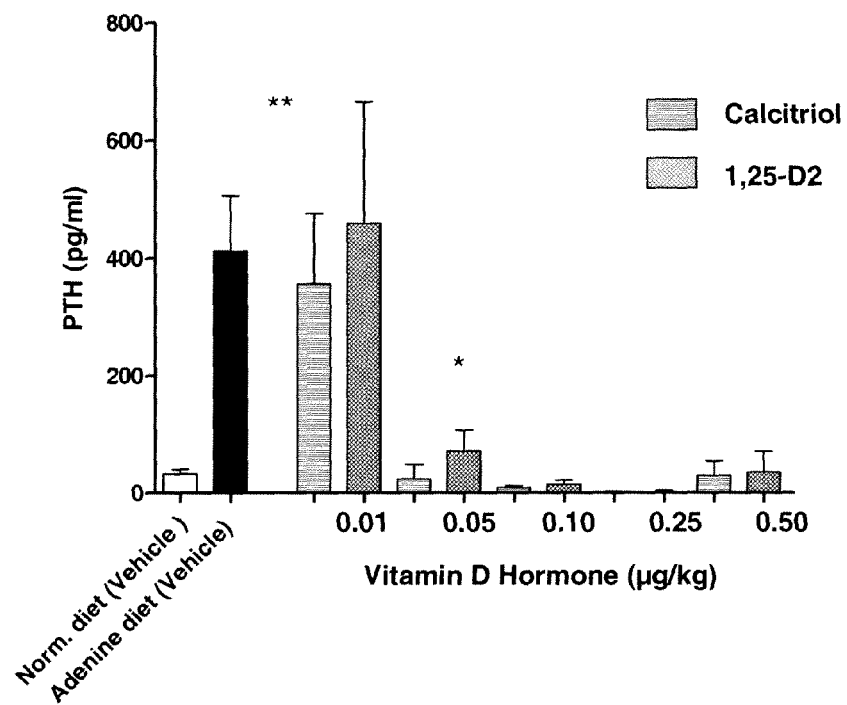
* - p<0.02 compared to adenine diet vehicle
** - p<0.0003 compared to normal diet vehicle
Figure 1
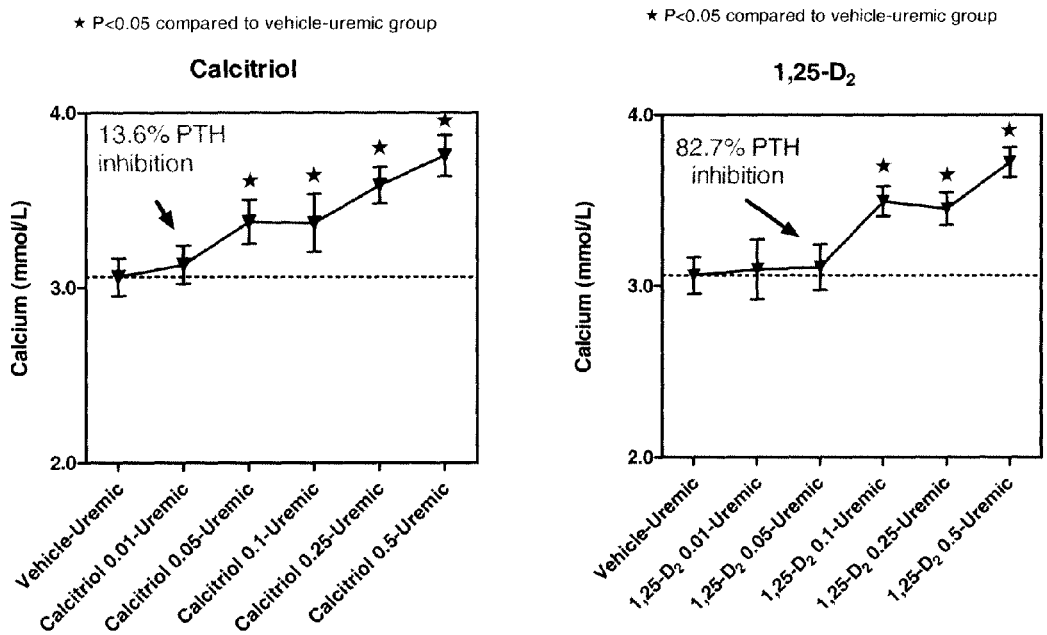
Figure 2
Figure 3

* p<0.05 vs. 0.5 μg/kg calcitriol

METHODS AND COMPOUNDS FOR VITAMIN D THERAPY

CROSS-REFERENCE TO RELATED APPLICATION

The benefit under 35 U.S.C. §119(e) of U.S. Provisional Patent Application Ser. No. 60/913,848 filed Apr. 25, 2007, is hereby claimed.

BACKGROUND

1. Field of the Disclosure

The disclosure relates generally to methods and compounds for Vitamin D therapy. More particularly, the disclosure relates to compositions comprising 1,25-dihydroxyvitamin $D_2$ and methods of administration thereof in the treatment and prevention of disease.

2. Brief Description of Related Technology

Secondary hyperparathyroidism is a disorder which develops primarily because of Vitamin D deficiency. It is characterized by abnormally elevated blood levels of parathyroid hormone (PTH) and, in the absence of early detection and treatment, it becomes associated with parathyroid gland hyperplasia and a constellation of metabolic bone diseases. It is a common complication of chronic kidney disease (CKD), with rising incidence as CKD progresses. Secondary hyperparathyroidism can also develop in individuals with healthy kidneys, due to environmental, cultural or dietary factors which prevent adequate Vitamin D supply.

As to secondary hyperparathyroidism and its occurrence in CKD, there is a progressive loss of cells of the proximal nephrons, the primary site for the synthesis of the vitamin D hormones (collectively "1,25-dihydroxyvitamin D") from 25-hydroxyvitamin $D_3$ and 25-hydroxyvitamin $D_2$. In addition, the loss of functioning nephrons leads to retention of excess phosphorus which combined reduces the activity of the renal 25-hydroxyvitamin D-1α-hydroxylase, the enzyme which catalyzes the reaction to produce the D hormones. These two events account for the low serum levels of 1,25-dihydroxyvitamin D commonly found in patients with moderate to severe CKD when vitamin D supply is adequate.

Reduced serum levels of 1,25-dihydroxyvitamin D cause increased, and ultimately excessive, secretion of PTH by direct and indirect mechanisms. The resulting hyperparathyroidism leads to markedly increased bone turnover and its sequela of renal osteodystrophy, which may include a variety of other diseases, such as, osteitis fibrosa cystica, osteomalacia, osteoporosis, extraskeletal calcification and related disorders, e.g., bone pain, periarticular inflammation and Mockerberg's sclerosis. Reduced serum levels of 1,25-dihydroxyvitamin D can also cause muscle weakness and growth retardation with skeletal deformities (most often seen in pediatric patients).

"Vitamin D" is a term that refers broadly to the organic substances named Vitamin $D_2$, Vitamin $D_3$, Vitamin $D_4$, etc., and is sometimes used loosely to refer to their metabolites and hormonal forms that influence calcium and phosphorus homeostasis. "Vitamin D deficiency" is a term that broadly refers to reduced or low blood levels of Vitamin D, as defined immediately above.

The most widely recognized forms of Vitamin D are Vitamin $D_2$ (ergocalciferol) and Vitamin $D_3$ (cholecalciferol). Vitamin $D_2$ is produced in plants from ergosterol during sunlight exposure and is present, to a limited extent, in the human diet. Vitamin $D_3$ is generated from 7-dehydrocholesterol in human skin during exposure to sunlight and also is found, to a greater extent than Vitamin $D_2$, in the human diet, principally in dairy products (milk and butter), certain fish and fish oils, and egg yolk. Vitamin D supplements for human use consist of either Vitamin $D_2$ or Vitamin $D_3$.

Both Vitamin $D_2$ and Vitamin $D_3$ are metabolized into prohormones by one or more enzymes located in the liver. The involved enzymes are mitochondrial and microsomal cytochrome P450 (CYP) isoforms, including CYP27A1, CYP2R1. CYP3A4, CYP2J3 and possibly others. These enzymes metabolize Vitamin $D_2$ into two prohormones known as 25-hydroxyvitamin $D_2$ and 24(S)-hydroxyvitamin $D_2$, and Vitamin $D_3$ into a prohormone known as 25-hydroxyvitamin $D_3$. The two 25-hydroxylated prohormones are more prominent in the blood, and can be collectively referred to as "25-hydroxyvitamin D." Vitamin $D_2$ and Vitamin $D_3$ can be metabolized into their respective prohormones outside of the liver in certain epithelial cells, such as enterocytes, which contain the same (or similar) enzymes, but extrahepatic prohormone production probably contributes little to blood levels of 25-hydroxyvitamin D.

The rates of hepatic and extrahepatic production of the Vitamin D prohormones are not tightly regulated, and they vary mainly with intracellular concentrations of the precursors (Vitamin $D_2$ and Vitamin $D_3$). Higher concentrations of either precursor increase prohormone production, while lower concentrations decrease production. Hepatic production of prohormones is inhibited by high levels of 25-hydroxyvitamin D via a poorly understood mechanism apparently directed to prevention of excessive blood prohormone levels.

The Vitamin D prohormones are further metabolized in the kidneys into potent hormones by an enzyme known as CYP27B1 (or 25-hydroxyvitamin $D_3$-1α-hydroxylase) located in the proximal kidney tubule. The prohormones 25-hydroxyvitamin $D_2$ and 24(S)-hydroxyvitamin $D_2$ are metabolized into hormones known as 1α,25-dihydroxyvitamin $D_2$ and 1α,24(S)-dihydroxyvitamin $D_2$. Likewise, 25-hydroxyvitamin $D_3$ is metabolized into a hormone known as 1α,25-dihydroxyvitamin $D_3$ (or calcitriol). These hormones are released by the kidneys into the blood for systemic delivery. The two 1α,25-dihydroxylated hormones, usually far more prominent in the blood than 1α,24(S)-dihydroxyvitamin $D_2$, can be collectively referred to as "1,25-dihydroxyvitamin D." Vitamin D prohormones can be metabolized into hormones outside of the kidneys in keratinocytes, lung epithelial cells, enterocytes, cells of the immune system (e.g., macrophages) and certain other cells containing CYP27B1 or similar enzymes, but such extrarenal hormone production is incapable of sustaining normal blood levels of 1,25-dihydroxyvitamin D in advanced CKD.

Blood levels of 1,25-dihydroxyvitamin D are precisely regulated by a feedback mechanism which involves PTH. The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular Vitamin D receptors (VDR) and secrete PTH. The secreted PTH stimulates expression of renal CYP27B1 and, thereby, increases production of Vitamin D hormones. As blood concentrations of 1,25-dihydroxyvitamin D rise again, the parathyroid glands attenuate further PTH secretion. As blood PTH levels fall, renal production of Vitamin D hormones decreases. Rising blood levels of 1,25-dihydroxyvitamin D also directly inhibit further Vitamin D hormone production by CYP27B1.

PTH secretion can be abnormally suppressed in situations where blood 1,25-dihydroxyvitamin D concentrations become excessively elevated, as can occur in certain disorders such as sarcoidosis or as a result of bolus doses of Vitamin D hormone replacement therapies. Oversuppression of PTH secretion can cause or exacerbate disturbances in calcium homeostasis. The parathyroid glands and the renal CYP27B1 are exquisitely sensitive to changes in blood concentrations of Vitamin D hormones so that serum 1,25-dihydroxyvitamin D is tightly controlled, fluctuating up or down by less than 20% during any 24-hour period. In contrast to renal production of Vitamin D hormones, extrarenal production is not under precise feedback control.

Blood levels of 1,25-dihydroxyvitamin D and substrate 25-hydroxyvitamin D prohormone, and regulation thereof, can also be affected by vitamin D hormone analogs, such as 1α-hydroxyvitamin $D_2$ and 19-nor-1,25 dihydroxyvitamin $D_2$.

The Vitamin D hormones have essential roles in human health which are mediated by the intracellular VDR. In particular, the Vitamin D hormones regulate blood calcium levels by controlling intestinal absorption of dietary calcium and reabsorption of calcium by the kidneys. The Vitamin D hormones also participate in the regulation of cellular differentiation and growth and normal bone formation and metabolism. Further, Vitamin D hormones are required for the normal functioning of the musculoskeletal, immune and renin-angiotensin systems. Numerous other roles for Vitamin D hormones are being postulated and elucidated, based on the documented presence of intracellular VDR in nearly every human tissue. For example, vitamin D has been postulated to play a role in cellular differentiation and cancer, in regulation of the immune system (immune enhancing or immune suppressing effects, depending on the situation), and atherosclerosis. Vitamin D deficiency increases the risk of many common cancers, multiple sclerosis, rheumatoid arthritis, hypertension, cardiovascular heart disease, and type I diabetes.

The actions of Vitamin D hormones on specific tissues depend on the degree to which they bind to (or occupy) the intracellular VDR in those tissues. VDR binding increases as the intracellular concentrations of the hormones rise, and decreases as the intracellular concentrations fall. In all cells, intracellular concentrations of the Vitamin D hormones change in direct proportion to changes in blood hormone concentrations. In cells containing CYP27B1 (or similar enzymes), intracellular concentrations of the Vitamin D hormones also change in direct proportion to changes in blood and/or intracellular prohormone concentrations, as discussed above.

Vitamin $D_2$, Vitamin $D_3$ and their prohormonal forms have affinities for the VDR which are estimated to be at least 100-fold lower than those of the Vitamin D hormones and do not effectively activate the receptor. As a consequence, physiological concentrations of these hormone precursors exert little, if any, biological actions without prior metabolism to Vitamin D hormones. However, supraphysiological levels of these hormone precursors, especially the prohormones, in the range of 10 to 1,000 fold higher than normal, can sufficiently occupy the VDR and exert actions like the Vitamin D hormones.

Blood levels of Vitamin $D_2$ and Vitamin $D_3$ are normally present at stable concentrations in human blood, given a sustained, adequate supply of Vitamin D from sunlight exposure and an unsupplemented diet. Slight, if any, increases in blood Vitamin D levels occur after meals since unsupplemented diets have low Vitamin D content, even those containing foods fortified with Vitamin D. The Vitamin D content of the human diet is so low that the National Institutes of Health (NIH) cautions "it can be difficult to obtain enough Vitamin D from natural food sources" [NIH, Office of Dietary Supplements, Dietary Supplement Fact Sheet: Vitamin D (2005)]. Almost all human Vitamin D supply comes from fortified foods, exposure to sunlight or from dietary supplements, with the last source becoming increasingly important. Blood Vitamin D levels rise only gradually, if at all, after sunlight exposure since cutaneous 7-dehydrocholesterol is modified by UV radiation to pre-Vitamin $D_3$ which undergoes thermal conversion in the skin to Vitamin $D_3$ over a period of several days before circulating in the blood.

Blood Vitamin D hormone concentrations also remain generally constant through the day in healthy individuals, but can vary significantly over longer periods of time in response to seasonal changes in sunlight exposure or sustained alterations in Vitamin D intake. Marked differences in normal Vitamin D hormone levels are commonly observed between healthy individuals, with some individuals having stable concentrations as low as approximately 20 pg/mL and others as high as approximately 70 pg/mL. Due to this wide normal range, medical professionals have difficulty interpreting isolated laboratory determinations of serum total 1,25-dihydroxyvitamin D; a value of 25 pg/mL may represent a normal value for one individual or a relative deficiency in another.

Transiently low blood levels of 1,25-dihydroxyvitamin D stimulate the parathyroid glands to secrete PTH for brief periods ending when normal blood Vitamin D hormone levels are restored. In contrast, chronically low blood levels of 1,25-dihydroxyvitamin D continuously stimulate the parathyroid glands to secrete PTH, resulting in a disorder known as secondary hyperparathyroidism. Chronically low hormone levels also decrease intestinal calcium absorption, leading to reduced blood calcium concentrations (hypocalcemia) which further stimulate PTH secretion. Continuously stimulated parathyroid glands become increasingly hyperplastic and eventually develop resistance to regulation by vitamin D hormones. Without early detection and treatment, secondary hyperparathyroidism progressively increases in severity, causing debilitating metabolic bone diseases, including osteoporosis and renal osteodystrophy.

Chronically low blood levels of 1,25-dihydroxyvitamin D develop when there is insufficient renal CYP27B1 to produce the required supply of Vitamin D hormones, a situation which commonly arises in CKD. The activity of renal CYP27B1 declines as the Glomerular Filtration Rate (GFR) falls below approximately 60 ml/min/1.73 m$^2$ due to the loss of functioning nephrons. In end-stage renal disease (ESRD), when the kidneys fail completely and hemodialysis is required for survival, renal CYP27B1 often becomes altogether absent. Any remaining CYP27B1 is greatly inhibited by elevated serum phosphorous (hyperphosphatemia) caused by inadequate renal excretion of dietary phosphorous.

Chronically low blood levels of 1,25-dihydroxyvitamin D also develop because of a deficiency of Vitamin D prohormones, since renal hormone production cannot proceed without the required precursors. Prohormone production declines markedly when cholecalciferol and ergocalciferol are in short supply, a condition often described by terms such as "Vitamin D insufficiency," "Vitamin D deficiency," or "hypovitaminosis D." Therefore, measurement of 25-hydroxyvitamin D levels in blood has become the accepted method among healthcare professionals to monitor Vitamin D status. Recent studies have documented that the great majority of CKD patients have low blood levels of 25-hydroxyvitamin D, and that the prevalence of Vitamin D insufficiency and deficiency increases as CKD progresses.

It follows that individuals most vulnerable to developing chronically low blood levels of 1,25-dihydroxyvitamin D are those with CKD. Most CKD patients typically have decreased levels of renal CYP27B1 and a shortage of 25-hydroxyvitamin D prohormones. Not surprisingly, most CKD patients develop secondary hyperparathyroidism. Unfortunately, early detection and treatment of secondary hyperparathyroidism in CKD is rare, let alone prevention.

The National Kidney Foundation (NKF) has recently focused the medical community's attention on the need for early detection and treatment of secondary hyperparathyroidism by publishing Kidney Disease Outcomes Quality Initiative (K/DOQI) Clinical Practice Guidelines for Bone Metabolism and Disease in Chronic Kidney Disease [*Am. J. Kidney Dis.* 42:S1-S202, 2003)]. The K/DOQI Guidelines identified the primary etiology of secondary hyperparathyroidism as chronically low blood levels of 1,25-dihydroxyvitamin and recommended regular screening in CKD Stages 3 through 5 for elevated blood PTH levels relative to Stage-specific PTH target ranges. CKD Stage 3 was defined as moderately decreased kidney function (GFR of 30-59 mL/min/1.73 m$^2$) with an intact PTH (iPTH) target range of 35-70 pg/mL; Stage 4 was defined as severely decreased kidney function (GFR of 15-29 mL/min/1.73 m$^2$), with an iPTH target range of 70-110 pg/mL; and Stage 5 was defined as kidney failure (GFR of <15 mL/min/1.73 m$^2$ or dialysis) with an iPTH target range of 150-300 pg/mL. In the event that screening revealed an iPTH value to be above the ranges targeted for CKD Stages 3 and 4, the Guidelines recommended a follow-up evaluation of serum total 25-hydroxyvitamin D to detect possible Vitamin D insufficiency or deficiency. If 25-hydroxyvitamin D below 30 ng/mL was observed, the recommended intervention was Vitamin D repletion therapy using orally administered ergocalciferol. If 25-hydroxyvitamin D above 30 ng/mL was observed, the recommended intervention was Vitamin D hormone replacement therapy using known oral or intravenous Vitamin D hormones or analogs. The Guidelines did not recommend the concurrent application of Vitamin D repletion and Vitamin D hormone replacement therapies, consistent with warnings mandated by the Food and Drug Administration in package inserts for Vitamin D hormone replacement products.

The NKF K/DOQI Guidelines defined Vitamin D sufficiency as serum 25-hydroxyvitamin D levels ≥30 ng/mL. Recommended Vitamin D repletion therapy for patients with "Vitamin D insufficiency," defined as serum 25-hydroxyvitamin D of 16-30 ng/mL, was 50,000 IU per month of oral Vitamin $D_2$ for 6 months, given either in single monthly doses or in divided doses of approximately 1,600 IU per day. Recommended repletion therapy for patients with "Vitamin D deficiency" was more aggressive: for "mild" deficiency, defined as serum 25-hydroxyvitamin D of 5-15 ng/mL, the Guidelines recommended 50,000 IU per week of oral Vitamin $D_2$ for 4 weeks, followed by 50,000 IU per month for another 5 months; for "severe" deficiency, defined as serum 25-hydroxyvitamin D below 5 ng/mL, the Guidelines recommended 50,000 IU/week of oral Vitamin $D_2$ for 12 weeks, followed by 50,000 IU/month for another 3 months. Doses of 50,000 IU per week are approximately equivalent to 7,000 IU per day.

Most concepts of vitamin D metabolism and function have been developed with the rat and/or chick as experimental models. Studying vitamin D metabolism is hampered by the paucity of data on the normal circulating levels of vitamin D metabolites in mammals under normal conditions. Most recent research has focused on the analysis of 25-hydroxyvitamin D and 1,25-dihydroxyvitamin D as indicators of vitamin D status or aberrant physiological states.

Shortly after the discovery of vitamin $D_2$ it seemed apparent that Vitamins $D_2$ and $D_3$ had similar biological activities in most mammals. More recent research, fostered by the discovery of sensitive analytical techniques and the availability of high specific activity $^3$H-labeled vitamin D species, indicated that differences in the metabolism of Vitamins $D_2$ and $D_3$ in mammals are perhaps widespread. Most notable were the apparent discrimination against Vitamin $D_2$ by pigs [Biochem J. 204:185-189], cows [J Nutr 113:2595-2600], and humans [Gene Regulation, Structure-Function Analysis and Clinical Application, Walter de Gruyter. Berlin, pp. 765-766] and the apparent preference of Vitamin $D_2$ by rats [Biochem J 204: 185-189, J Bone Miner Res 5(Supplement 2):S265].

Vitamin D and its metabolites are transported in the blood of vertebrates attached to Vitamin D binding protein (DBP). Baird et al [Recent Prog Horm Res. 25:611-664] have shown that protein binding increases the solubility of steroids and that the metabolic clearance rate of steroids is in part dependent on their binding to specific plasma proteins.

Hay and Watson [Comp Biochem Physiol 56B:375-380] studied the affinities of DBP for 25-hydroxyvitamin $D_2$ and 25-hydroxyvitamin $D_3$ in 63 vertebrate species. They found that many of the studied species discriminated against 25-hydroxyvitamin $D_2$ in favor of 25-hydroxyvitamin $D_3$ [Biochem J 204:185-189]. However, in rats the discrimination is against Vitamin $D_3$ in favor of Vitamin $D_2$. The rat DBP is known to have equal affinity for 25-hydroxyvitamin $D_2$ and 25-hydroxyvitamin $D_3$, but a lower affinity for Vitamin $D_2$ relative to Vitamin $D_3$ [Steroids 37:581-592]. Reddy et al., [Calci Tissue Int 36:524] suggested that the lower affinity for Vitamin $D_2$ resulted in its enhanced availability for liver 25-hydroxylation. Hence, in the presence of DBP, more 25-hydroxyvitamin $D_2$ was made relative to 25-hydroxyvitamin $D_3$ when equal amounts of Vitamin $D_2$ or Vitamin $D_3$ substrate were perfused into rat livers. In the experiments conducted by Reddy et al., if binding protein was eliminated from the perfusion media, equal amounts of 25-hydroxyvitamin $D_2$ and 25-hydroxyvitamin $D_3$ were synthesized. Collectively, these data suggest that discrimination against the different forms of Vitamin D could likely result from variations in the affinity of DBP for the parent compound and/or one or more of their metabolites. Regardless of the mechanism for discrimination, it appears that these differences are present to afford the species the most efficient utilization of the most abundant Vitamin D metabolites available in their environment.

Critical questions remain unanswered regarding complete elucidation of the Vitamin $D_2$ metabolic pathway, and species differences between Vitamin $D_2$ and $D_3$ metabolism are still virtually unexplored. The introduction of Vitamin D as a pharmacological intervention has resulted in a totally different set of issues regarding their metabolism, tissue kinetics, mechanism of action, and potential therapeutic uses.

Vitamin D receptors are present throughout the human body in a wide variety of cells, and there have been reports that vitamin D hormone has diverse "non-classical" biologic effects on cellular proliferation, the immune system and the cardiovascular system, beyond its "classical" effects on the PTH system. It has also been reported that 25-hydroxyvitamin $D_2$ has direct effects on parathyroid cells in suppressing PTH [Kidney International, 70(4):654-659, August 2006]. There has been one report that Vitamin $D_2$ was less than one-third as potent as Vitamin $D_3$ and exhibited a shorter duration of action relative to Vitamin $D_3$; administration of 50,000 IU of ergocalciferol or cholecalciferol to healthy male humans produced similar rises in serum concentration of the administered vitamin, indicating equivalent absorption, but 25-hydroxyvitamin $D_3$ levels peaked at 14 days whereas 25-hydroxyvitamin $D_2$ levels fell early and were not different from baseline at 14 days [J. Clin. Endocrinol. Metab., 89(11): 5387-5391 (2004)].

Thus, the relative contribution of 25-hydroxyvitamin D compounds and 1,25-dihydroxyvitamin D compounds to PTH suppression, the relative potency of 1,25-dihydroxyvitamin $D_2$ and 1,25-dihydroxyvitamin $D_3$ in vivo, and the spectrum of non-classical biological effects of each of these hormones has not clearly been elucidated. There remains a need for alternative vitamin D hormone therapies that ideally provide beneficial effects on PTH levels, immune status and/or cardiovascular health, with reduced toxicity.

SUMMARY

In one aspect the disclosure provides a method of increasing or maintaining blood concentrations of 1,25-dihydroxyvitamin D in a patient by administering an amount of 1,25-dihydroxyvitamin As noted hereinbefore, many conditions can lead to 1,25-dihydroxyvitamin D deficiencies, including living in northern latitudes. Treatment with 1,25-dihydroxyvitamin $D_2$ of those patients in need thereof can provide blood concentrations of 1,25-dihydroxyvitamin D that are increased or maintained within a patient's normal historical range for 1,25-dihydroxyvitamin D. Such administration can be accomplished without a substantially increased risk of hypercalcemia, hyperphosphatemia, or over suppression of plasma intact parathyroid hormone (PTH), all of which have been recognized as risks when treatment with a vitamin D compound is incurred. Moreover, blood levels of 1,25-dihydroxyvitamin D can be maintained in the patient's historical physiological range between doses, eliminating spike and trough concentration patterns. In another aspect, the disclosure provides a method of administering an amount of 1,25-dihydroxyvitamin $D_2$ such that one or more symptoms of 1,25-dihydroxyvitamin D deficiency are alleviated, for example, symptoms of deficiency in the non-classical effects of vitamin D.

In yet another aspect, the disclosure provides a method which has one or more of the following effects: concurrently lowering or maintaining plasma intact parathyroid hormone levels; increasing or maintaining serum calcium levels; maintaining serum phosphorous levels; increasing serum 1,25-dihydroxyvitamin D levels; and maintaining serum 1,25-dihydroxyvitamin D levels, in a human patient, by administering to the patient an effective amount of 1,25-dihydroxyvitamin $D_2$ according to the disclosure herein. Many diseases manifest abnormal levels of more than one hormone and mineral. In $CKD_2$ for example, patients may experience decreases in 1,25-dihydroxyvitamin D, increases in PTH, and increases in serum phosphorous. Treatment in accordance with the disclosure can provide concurrent leveling and/or maintaining of these various hormone and mineral levels.

The disclosure herein provides a method for treating and/or preventing hyperparathyroidism secondary to chronic kidney disease by lowering (or maintaining low) serum parathyroid hormone (PTH) levels in a human patient suffering from the disease by administering to the patient an effective amount of 1,25-dihydroxyvitamin $D_2$ according to the disclosure herein. The method may ameliorate or prevent the renal osteodystrophy which can develop in such patients.

In one aspect, a method for lowering or maintaining lowered serum parathyroid hormone in human patients includes administering to said patients a therapeutically effective amount of 1,25-dihydroxyvitamin $D_2$ according to the disclosure herein to lower or maintain lowered serum parathyroid hormone levels, preferably an amount that lowers PTH levels by at least 15%, 20%, 25% or 30%, or alternatively the amount need to reduce serum levels of PTH to the target range for the CKD Stage (e.g., for Stage 3 is 35-70 pg/mL (equivalent to 3.85-7.7 pmo)/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1)).

In another aspect, the method includes administering to a patient suffering from hyperparathyroidism secondary to chronic kidney disease (Stage 3, 4 or 5) an effective amount of 1,25-dihydroxyvitamin $D_2$ according to the disclosure herein to lower the serum PTH level. For secondary hyperparathyroidism as well as other therapies, the 1,25-dihydroxyvitamin $D_2$ is contemplated to be administered in an amount of 0.1 µg per week to about 100 µg per week, for example.

The disclosure herein also provides a pharmaceutical composition having serum (or plasma) PTH lowering activity, which includes, in unit dosage form, an effective amount of 1,25-dihydroxyvitamin $D_2$ undo pharmaceutically acceptable excipient.

The treatment method described herein is an alternative to conventional vitamin D replacement therapy with 1,25-dihydroxyvitamin $D_3$, 1α-hydroxyvitamin $D_3$, 19-nor-1,25-dihydroxyvitamin $D_2$, and other active vitamin D analogs.

In embodiments, the method is characterized by providing an active vitamin D compound which has safety and patient survival benefits associated with other vitamin $D_2$ compounds, but which, in addition, is able to replace the classical and non-classical functions of 1,25-dihydroxyvitamin $D_3$ more completely than known synthetic alternatives. As such, the method addresses a long felt need in therapy for secondary hyperparathyroidism and other conditions associated with vitamin D insufficiency or deficiency.

The methods and compositions are contemplated to be associated with one or more benefits, such as significantly: increasing the bioavailability of the contained 1,25-dihydroxyvitamin $D_2$ by promoting absorption directly into the bloodstream rather than into the lymphatic system via chylomicrons; increasing the bioavailability of the contained 1,25-dihydroxyvitamin $D_2$ by reducing catabolism in the enterocytes of the upper small intestine; decreasing the undesirable first pass effects of the contained 1,25-dihydroxyvitamin $D_2$ on the duodenum; avoiding production of adverse supraphysiologic surges in blood levels of 1,25-dihydroxyvitamin D; preventing reduction of blood concentrations of 1,25-dihydroxyvitamin D below optimal levels; restoring blood concentrations of 1,25-dihydroxyvitamin D to optimal levels; maintaining blood concentrations of 1,25-dihydroxyvitamin D at such optimal levels; decreasing disruptions in Vitamin D metabolism and related aberrations in PTH, calcium and phosphorus homeostasis; and decreasing the risk of serious side effects associated with Vitamin D hormone replacement, including hypercalciuria, hypercalcemia, hyperphosphatemia, and Vitamin D toxicity.

In another aspect, the invention provides a method effective to restore and maintain blood concentrations of 1,25-dihydroxyvitamin D in human suffering from chronic kidney disease (Stage 3, 4 or 5) through chronic treatment (e.g., at least 30 days, or 2, 3, 4, 5 or 6 months, or continued therapy through life), while avoiding progressive loss of 25-hydroxyvitamin D and 1,25-dihydroxyvitamin $D_3$. In exemplary embodiments, treatment of a human with chronic kidney disease suffering from 1,25-dihydroxyvitamin D insufficiency or deficiency, is contemplated.

The methods described herein are also intended to be used in the treatment or prevention of conditions in humans including, but not limited to: bone depletive disorders which respond to administration of active forms of vitamin D; immunoresponsive disorders which respond to administration of active forms of vitamin D; high blood pressure; bacterial infection; and cardiovascular disease malabsorption disorders, cancers, and 1,25-dihydroxyvitamin D insufficiency and deficiency. Expected beneficial effects include amelioration of the disorder.

In summary, various aspects of the disclosure can provide therapeutic methods for preventing and/or treating conditions associated with low blood concentrations of 1,25-dihydroxyvitamin D, elevated concentrations of PTH, elevated concentrations of serum phosphorous, and low concentrations of serum calcium. The methods are suitable for lowering elevated blood parathyroid hormone levels, and/or maintaining lowered blood PTH levels in subjects while maintaining normalized or targeted levels of serum calcium, serum phosphorous, and serum 1,25-dihydroxyvitamin $D_2$. The methods described herein also include reducing the risk of over suppression of PTH by administering to a subject in need thereof an amount of 1,25-dihydroxyvitamin $D_2$ to lower or maintain PTH levels while avoiding or preventing low bone turnover rate, i.e. adynamic bone disease.

Further aspects and advantages will be apparent to those of ordinary skill in the art from a review of the following detailed description. While the methods and compositions are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, twelve drawing figures are appended hereto.

FIG. 1 shows measured iPTH levels in control, calcitriol, and 1,25-dihydroxyvitamin $D_2$-treated rats having adenine-induced kidney failure according to Example 3.

FIG. 2 shows measured serum calcium levels for calcitriol-treated animals, and

FIG. 3 shows measured serum calcium levels for 1,25-dihydroxyvitamin $D_2$-treated animals, according to Example 3.

Figure 4:
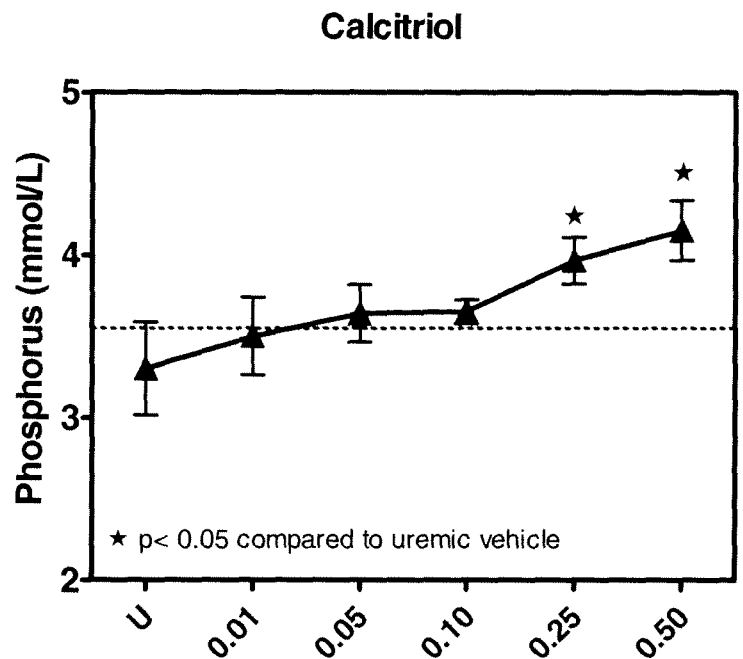
FIG. 4 shows measured serum phosphorous levels for calcitriol-treated animals.

DETAILED DESCRIPTION 1,25-dihydroxyvitamin $D_2$ has several important potential advantages over current therapies for the treatment of chronic kidney disease (CKD). 1,25-dihydroxyvitamin $D_2$ belongs to the class of $D_2$ analogs which includes 19-nor-1,25-dihydroxyvitamin $D_2$.

However, 19-nor-1,25-dihydroxyvitamin $D_2$ has an important A-ring modification which is believed to result in altered interactions with the vitamin D receptor, and therefore differential gene expression compared to 1,25-dihydroxyvitamin $D_2$ and 1,25-dihydroxyvitamin $D_3$. Chronic treatment with 19-nor-1,25-dihydroxyvitamin $D_2$ leads to decreased levels of 1,25-dihydroxyvitamin $D_3$. Also after a period of treatment (24-48 hours), with 19-nor-1,25-dihydroxyvitamin $D_2$, tissues become differentially sensitized to the activity of the compound. For example, low calcemic activity of 19-nor-1,25-dihydroxyvitamin $D_2$ has been attributed to reduced sensitivity of intestine and bone due to changes in the metabolic activity of these tissues.

19-Nor-1,25-dihydroxyvitamin $D_2$ is approximately 10-fold less potent than 1,25-dihydroxyvitamin $D_3$ in promoting bone resorption in vivo. Yet in vitro studies examining markers of bone metabolism indicate that the effects of 19-nor-1,25-dihydroxyvitamin $D_2$ and 1,25-dihydroxyvitamin $D_3$ in culture on VDR expression, suppression of cell proliferation, regulation of osteocalcin and alkaline phosphatase activity are indistinguishable. Conversely, however, in a study using Caco-2 cells 19-nor-1,25-dihydroxyvitamin $D_2$ did not show a significant effect on calcium transport, while 1,25-dihydroxyvitamin $D_3$ stimulated calcium transport by 934%. Also, 19-nor-1,25-dihydroxyvitamin $D_2$ exhibits differential regulation of the CYP3A9 gene at the transcriptional level.

Without intending to be bound by any particular theory, it is believed that at the level of the VDR, there are some distinctive interactions with 19-nor-1,25-dihydroxyvitamin $D_2$ that result in the altered ability of VDR to act on the transcriptional regulation of certain genes. Accordingly, it is believed that 19-nor-1,25-dihydroxyvitamin $D_2$ is not able to fully replace all of the functions of 1,25-dihydroxyvitamin $D_3$.

All major circulating vitamin D metabolites bind to DBP and or albumin or lipoprotein. Normally, DBP occupancy by vitamin D metabolites is approximately 2%. While some studies have determined that metabolites of 25-hydroxyvitamin $D_3$, such as 24,25-dihydroxyvitamin $D_3$, 1,24,25-trihydroxyvitamin $D_3$, and 1,25-dihydroxyvitamin $D_3$ have higher affinity for DBP than the corresponding $D_2$ metabolites, a more recent study of human DBP indicates that metabolites of $D_2$ have equivalent, or only slightly lower affinity for DBP than those of vitamin $D_3$ metabolites. Accordingly, there is believed to be no significant difference between 1,25-dihydroxyvitamin $D_2$ and 1,25-dihydroxyvitamin $D_3$ with respect to DBP binding.

In contrast, 19-nor-1,25-dihydroxyvitamin $D_2$ has a lower (3-fold) affinity for DBP compared to 1,25-dihydroxyvitamin $D_3$. This latter observation may account for the shortened half-life of 19-nor-1,25-dihydroxyvitamin $D_2$ (between 4-6 hours in healthy patients compared to 15 hours in patients with chronic renal failure and 20 hours in patients with Stage 4 CKD). A short half-life is believed to be detrimental to patients over the long term, since the hormone spike may be followed by a period of "vitamin D deficiency" as induction of CYP24 depletes stores of normal vitamin D hormone and prohormone. Furthermore, a sustained release delivery system, as described below, is desirable.

Since 19-nor-1,25-dihydroxyvitamin $D_2$, 1,25-dihydroxyvitamin $D_3$ and 1,25-dihydroxyvitamin $D_2$ all induce CYP24, chronic treatment with any of these agents will result in progressive loss of 25-hydroxyvitamin $D_3$ and 1,25-dihydroxyvitamin $D_3$. It is therefore important that over the long term, the vitamin D hormone used for replacement therapy can replace all of the classical, as well as the non-classical functions of Vitamin $D_3$ hormone. Vitamin $D_2$ has been used as a nutritional substitute for vitamin $D_3$. 1,25-dihydroxyvitamin $D_2$ is believed to have advantages over 1,25-dihydroxyvitamin $D_3$ based on safety and patient survival benefits. Further, 1,25-dihydroxyvitamin $D_2$ is believed to have advantages over 19-nor-1,25-dihydroxyvitamin $D_2$ and other vitamin D hormone analogs because it is more completely able to replace the classical and non-classical functions of 1,25-dihydroxyvitamin $D_3$.

As described above, differential gene regulation by 19-nor-dihydroxyvitamin $D_2$ and acquired resistance to this compound in certain tissues such as intestine and kidney, coupled with treatment-induced CYP24 depletion of 25-hydroxyvitamin $D_3$ and 1,25-dihydroxyvitamin $D_3$ may have a net effect over the long term of treatment of vitamin D deficiency for certain vitamin D-dependent functions. For example, the reduced efficacy of 19-nor-dihydroxyvitamin $D_2$ in stimulating osteoclast function may be an important consideration over long term therapy, since regulation of osteoclast function is critical for bone remodeling. Changes in bone remodeling dynamics could eventually alter the structural integrity of bone. Accordingly 1,25-dihydroxyvitamin $ID_2$ is believed to have significant benefits for long term hormone replacement therapy based on its closer biochemical and physiological equivalence to 1,25-dihydroxyvitamin $D_3$, with an increased comparative patient survival benefit.

In one embodiment, administration of 1,25-dihydroxyvitamin $D_2$ according to the methods and compositions described herein will show physiological equivalence to 1,25-dihydroxyvitamin $D_3$, with an increased safety. In another embodiment, For example, serum calcium (Ca) levels can be compared by techniques known in the art to assess safety. As another example, inorganic phosphate (Pi) levels can be compared by techniques known in the art to assess safety. Plasma intact parathyroid hormone (iPTH) levels can be compared by techniques known in the art to assess efficacy.

As described above, 1,25-dihydroxyvitamin $D_3$ has diverse "non-classical" biologic effects beyond its "classical" effects on the PTH system, such as effects on cellular proliferation, the immune system and the cardiovascular system. Administration of 1,25-dihydroxyvitamin $D_2$ according to the methods and compositions described herein will preferably have one or more analogous effects.

In one embodiment, administration of 1,25-dihydroxyvitamin $D_2$ as described herein will contribute one or more non-classical effects on the renin-angiotensin system typically shown by 1,25-dihydroxyvitamin $D_3$. For example, in one type of embodiment administration of 1,25-dihydroxyvitamin $D_2$ as described herein will provide negative endocrine regulation of the renin-angiotensin system.

In another embodiment, administration of 1,25-dihydroxyvitamin $D_2$ as described herein will contribute one or more non-classical effects on bone typically shown by 1,25-dihydroxyvitamin $D_3$, such as calcium and phosphate homeostasis. The effect of administration of 1,25-dihydroxyvitamin $D_2$ can be compared with respect to direct and indirect effects on bone. For example, the effects on regulation of calcium flux, osteocalcin and acid and alkaline phosphatase activity, and interleukin-6 (IL-6) can be determined. Effects on bone mineralization can be determined directly in animal models.

In still another embodiment, administration of 1,25-dihydroxyvitamin $D_2$ as described herein will contribute one or more non-classical effects on immunomodulatory activity typically shown by 1,25-dihydroxyvitamin D3. Immuno- regulatory properties of 1,25-dihydroxyvitamin $D_3$ have been demonstrated in different models of autoimmune diseases. For example, 1,25-dihydroxyvitamin $D_3$ has been shown to inhibit in vitro differentiation and maturation of dendritic cells, has been shown to effect induction of T cell hyporesponsiveness, to effect stimulation of human peripheral blood lymphocytes (PBL), to inhibited the growth-promoting lymphokine interleukin-2, and to inhibit the proliferation of mitogen-activated lymphocytes.

The person of ordinary skill in the art will be able to determine methods for detecting effects such as those described above. In addition, comparison of genes regulated by gene array microchip analysis is also contemplated.

As used herein, the term "Vitamin D toxicity" is meant to refer to the side effects suffered from excessively elevated Vitamin D blood levels, including one or more of nausea, vomiting, polyuria, hypercalciuria, hypercalcemia and hyperphosphatemia.

"Vitamin D insufficiency and deficiency" is generally defined as having serum 25-hydroxyvitamin D levels below 30 ng/mL (see National Kidney Foundation guidelines, NKF, Am. J. Kidney Dis. 42:S1-S202 (2003), incorporated herein by reference).

As used herein the term "hypercalcemia" refers to condition in a patient wherein the patient has corrected serum levels of calcium above 10.2 mg/dL. Normal corrected serum levels of calcium for a human are between about 8.6 to 10.2 mg/dL.

As used herein the term "hyperphosphatemia" refers to a condition in a patient having normal kidney function, or Stage 3-4 CKD, wherein the patient has serum phosphorous levels above 4.6 mg/dL. In a patient who has Stage 5 CKD, hyperphosphatemia occurs when the patient has serum levels above 5.5 mg/dL. Normal values for serum phosphorous in a human are 2.5-4.5 mg/dL.

As used herein the term "over suppression of plasma iPTH" refers to a condition in a patient having normal kidney function, or Stage 1-3 CKD, wherein the patient has levels of plasma iPTH below 15 pg/mL. In a patient having Stage 4 CKD, over suppression of plasma iPTH occurs when the patient has levels of plasma iPTH below 30 pg/mL. In a patient having Stage 5 $CKD_2$ over suppression of plasma iPTH occurs when the patient has levels of plasma iPTH below 100 pg/mL.

As used herein, the term "Vitamin D hormone replacement therapy" refers to the administration to a patient of an effective amount of 1,25-dihydroxyvitamin $D_2$, optionally together with or other metabolites and analogs of Vitamin D which can substantially occupy the intracellular VDR. Preferably the administration of active vitamin D is by 1,25-dihydroxyvitamin $D_2$ alone.

As used herein, the term "substantially constant" with respect to the serum or blood level of 1,25-dihydroxyvitamin $D_2$ preferably means that the release profile of the controlled release formulation should not include increases in total serum or blood levels of 1,25-dihydroxyvitamin $D_2$ of greater than approximately 75 pg/mL each after administration of a unit dose, optionally over a period of preferably at least 30 minutes or 4 hours, etc.

As used herein, the term "controlled release," "sustained release," and "modified release" are used interchangeably, and refer to the release of the administered 1,25-dihydroxyvitamin $D_2$ in a way that deviates from immediate release. The term "controlled release" optionally includes delayed release characteristics. For example, a delayed release type of controlled release formulation will be characterized by Cmax at a time greater than Cmax for an immediate release formulation. As another example, a sustained release type of controlled release formulation will be characterized by release at such a rate that total serum or blood levels of 1,25-dihydroxyvitamin $D_2$ are maintained or elevated above predosing levels for an extended period of time, e.g. 20 to 40 minutes or 1 to 15 hours or even longer.

"Supraphysiologic" in reference to intralumenal, intracellular and blood levels of Vitamin D refers to a total concentration of 1,25-dihydroxyvitamin D markedly greater than the generally stable levels observed in a Vitamin D-replete subject, animal or human patient over the course of any 24-hour period by laboratory measurement when Vitamin D supplementation has been withheld for at least 30 days. "Adverse supraphysiologic surge" refers to a local or serum concentration of 1,25-dihydroxyvitamin D that elicits adverse effects such as excessive extrarenal hormone production, leading to local adverse effects on calcium and phosphorus metabolism, inhibition of hepatic 25-hydroxylation of vitamin D, increased catabolism of both Vitamin D and 25-hydroxyvitamin D, hypercalciuria, hypercalcemia and/or hyperphosphatemia, with possible cardiovascular sequelae.

The term "therapeutically effective amount" depends on the patient's condition and is an amount effective to achieve a desired clinical effect, e.g. to maintain a laboratory test value within the normal range or the recommended range for that patient's condition, or an amount effective to reduce the occurrence or severity of a clinical sign or symptom of disease. In some embodiments, a therapeutically effective amount is an amount effective on average to achieve at least a 15%, 20%, 25% or 30% reduction in serum parathyroid hormone levels (iPTH) from baseline levels without treatment. In yet other embodiments, a therapeutically effective amount is an amount effective on average to reach CKD Stage-specific iPTH target ranges, which for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1).

As used herein, the term "hyperparathyroidism" refers to primary hyperparathyroidism, secondary hyperparathyroidism and hyperparathyroidism secondary to chronic kidney disease (Stage 3, 4 or 5).

As used herein, the term "patient's normal historical physiological range of serum 1,25-dihydroxyvitamin D" refers to the average blood concentration range of 1,25-dihydroxyvitamin D of a patient based on at least two annual or biannual readings of serum 1,25-dihydroxyvitamin D levels taken while the kidneys are healthy.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

It is noted that the medical community currently views Vitamin $D_3$ compounds as biologically indistinguishable from the corresponding Vitamin $D_2$ compounds. This is evident from the indiscriminate inclusion of either Vitamin $D_2$ or $D_3$ in vitamin supplements prepared for human use, and from the interchangeable use of either vitamin in treating bone diseases caused by vitamin D deficiency. Curiously, medical experts consider the hormonally active forms of the two vitamins to be equivalent despite lack of confirmation from a single human study. (It is also interestingly noted that Vitamin $D_4$ is described in The Merck Index (Merck Index, 11th ed. (1989) p. 9932) as having doubtful biological activity.) As described herein, the 1,25-dihydroxyvitamin $D_2$ compound is useful as an active compound in a pharmaceutical composition. The hormone can be produced by any of the various known methods of isolation or synthesis. See, for example, U.S. Pat. No. 3,880,894 (Apr. 29, 1975).

The 1,25-dihydroxyvitamin $D_2$ hormone can be processed in accordance with conventional methods of pharmacy to produce pharmaceutical agents for administration to patients, e.g., in admixtures with conventional excipients such as pharmaceutically acceptable organic or inorganic carrier substances suitable for parenteral (e.g., subcutaneous, intravenous, intramuscular, and depot injection), and nonparenteral such as enteral (e.g., oral) or topical application which do not deleteriously react with the active compound. The hormone can also be administered in alternative fashions, including nasopharyngeal or mucosal absorption such as intranasally, intrarectally, and intravaginally.

Suitable pharmaceutically acceptable carriers include but are not limited to water, salt (buffer) solutions, alcohols, gum arabic, mineral and vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., fillers, lubricants, preservatives, stabilizers, wetting agents, emulsifiers, salts for influencing osmotic pressure, buffers, coloring, flavoring and/or aromatic active compounds. If a solid carrier is used, the dosage form of the 1,25-dihydroxyvitamin may be, for example, tablets, capsules, powders, suppositories, or lozenges. If a liquid carrier is used, soft gelatin capsules, transdermal patches, aerosol sprays, topical creams, syrups or liquid suspensions, emulsions and solutions are contemplated.

The presence of alcohol in a dosage form can interfere with the ability of 1,25-dihydroxyvitamin $D_2$ to bind to DBP. Accordingly, oral dosage forms free of or substantially free of alcohols are contemplated.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, etc.

For parenteral application, particularly suitable are injectable, sterile solutions, preferably oily or aqueous solutions, as well as suspensions, emulsions, and implants, including suppositories. Ampoules are convenient unit dosages. It is also possible to freeze-dry the 1,25-dihydroxyvitamin $D_2$ and store and use the lyophilizates obtained in preparation of products. For example, lyophilizates can be stored in a vial and used to reconstitute a solution for injection immediately before administration.

For enteral application, particularly suitable are tablets, dragees, liquids, drops, suppositories, and capsules. A syrup, elixir, or the like can be used wherein a sweetened vehicle is employed. For example, in a soft gelatin formulation the capsule fill suitably contains 1,25-dihydroxyvitamin $D_2$ dissolved in a pharmaceutically acceptable oil, e.g., fractionated coconut oil, and includes an antioxidant which may be, for example, butylated hydroxyanisole (BHA), butylated hydroxytoluene (BHT) or vitamin E. The capsule shell can suitably contain gelatin, glycerin, titanium dioxide and coloring agent. The fill is typically about 58-59% by weight of the whole capsule.

Where appropriate, 1,25-dihydroxyvitamin $D_2$ can be combined with one or more other active compounds, for example one or more agents characterized by the ability to reduce loss of bone mass, or bone mineral content in patients. Such compounds can include other vitamin D compounds, conjugated estrogens, sodium fluorides, bisphosphonates, cobalamin, pertussin toxin, or boron. The dosage forms may also contain adjuvants, such as preserving or stabilizing adjuvants.

Particularly preferred are oral and IV dosage forms.

Controlled release/sustained release compositions for dosage forms are contemplated. In one embodiment, an amount of 1,25-dihydroxyvitamin $D_2$ is included in a controlled release formulation and is orally administered to a human in need of treatment. For example, delayed release, sustained release, and delayed-sustained release compositions are contemplated.

A controlled release formulation of 1,25-dihydroxyvitamin $D_2$ will have one or more benefits, such as significantly: increasing the bioavailability of the contained 1,25-dihydroxyvitamin $D_2$ by promoting absorption directly into the bloodstream rather than into the lymphatic system via chylomicrons; increasing the bioavailability of the contained 1,25-dihydroxyvitamin $D_2$ by reducing catabolism in the enterocytes of the upper small intestine; decreasing the undesirable first pass effects of the contained 1,25-dihydroxyvitamin $D_2$, for example on the duodenum and/or jejunum; avoiding production of adverse supraphysiologic surges in blood levels of 1,25-dihydroxyvitamin D; increasing the effectiveness of orally administered 1,25-dihydroxyvitamin $D_2$ in restoring blood concentrations of 1,25-dihydroxyvitamin D to optimal levels (defined for CKD patients as equal to or greater than 25 pg/mL); increasing the effectiveness of orally administered 1,25-dihydroxyvitamin $D_2$ in maintaining blood concentrations of 1,25-dihydroxyvitamin D at such optimal levels (e.g., for at least 30 days); decreasing disruptions in Vitamin D metabolism and related aberrations in PTH, calcium and phosphorus homeostasis; and, decreasing the risk of serious side effects associated with Vitamin D hormone replacement, including hypercalciuria, hypercalcemia, hyperphosphatemia, and Vitamin D toxicity.

Similarly, an amount of 1,25-dihydroxyvitamin $D_2$ can be provided in an isotonic sterile formulation suitable for gradual intravenous administration. Gradual intravenous administration, can have one or more benefits, such as significantly: increasing the bioavailability of the contained 1,25-dihydroxyvitamin $D_2$ by promoting absorption directly into the bloodstream rather than into the lymphatic system via chylomicrons; increasing the bioavailability of the contained 1,25-dihydroxyvitamin $D_2$ by reducing catabolism in the enterocytes of the upper small intestine; decreasing the undesirable first pass effects of the contained 1,25-dihydroxyvitamin $D_2$ on the duodenum and jejunum; avoiding production of adverse supraphysiologic surges in blood levels of 1,25-dihydroxyvitamin D; increasing the effectiveness of IV administered 1,25-dihydroxyvitamin $D_2$ in restoring blood concentrations of 1,25-dihydroxyvitamin D to optimal levels (defined for CKD patients as equal to or greater than 25 pg/mL); increasing the effectiveness of orally administered 1,25-dihydroxyvitamin $D_2$ in maintaining blood concentrations of 1,25-dihydroxyvitamin D at such optimal levels (e.g., for at least 30 days); decreasing disruptions in Vitamin D metabolism and related aberrations in PTH, calcium and phosphorus homeostasis; and, decreasing the risk of serious side effects associated with Vitamin D hormone replacement, including hypercalciuria, hypercalcemia, hyperphosphatemia, and Vitamin D toxicity.

The preparation of a controlled release form of 1,25-dihydroxyvitamin $D_2$ suitable for oral administration can be carried out in accordance with many different principles of controlled release, and according to many different formulation techniques. For example, controlled release via dissolution control, diffusion control, and ion exchange are contemplated. Non-limiting examples include membrane encapsulated reservoir devices, bioerodible polymers, matrix systems, and osmotic systems. Liposomes can also be used as a controlled release carrier for the hormone. Temperature and/or pH can be used as triggers for release (e.g., temperature-dependent solubility of a coating or matrix, and/or pH-dependent solubility of a coating or matrix).

As one specific example, 1,25-dihydroxyvitamin $D_2$ can be embedded for controlled release in a polymer matrix of a biological degradable polymer, a water-soluble polymer or a mixture of both, and optionally suitable surfactants. Embedding can mean in this context the incorporation of microparticles in a matrix of polymers. Controlled release formulations can be obtained through encapsulation of dispersed micro-particles or emulsified micro-droplets (e.g., via known dispersion or emulsion coating technologies.

In another type of formulation, the controlled release dosage form includes a matrix which binds the 1,25-dihydroxyvitamin $D_2$ and permits a slow, relatively steady, preferably substantially constant, release of the 1,25-dihydroxyvitamin $D_2$ over a period of four to eight hours or more, by simple diffusion and/or gradual disintegration.

One type of embodiment includes a composition comprising a controlled release formulation of 1,25-dihydroxyvitamin $D_2$ and a method of administering such a formulation to treat 1,25-dihydroxyvitamin D insufficiency and deficiency at a level of efficiency heretofore unobtainable; without the undesirable first pass effects of the Vitamin D compounds on the duodenum; without adverse supraphysiological surges in intralumenal, intracellular and blood levels of 1,25-dihydroxyvitamin D and their consequences; and without serious side effects associated with Vitamin D supplementation, namely Vitamin D toxicity.

A preferred controlled release composition will be designed to maintain concentrations of 1,25-dihydroxyvitamin $D_2$ at or above 25 pg/mL, or in a range of about 25 pg/mL to about 65 pg/mL, and is prepared in such a manner as to effect controlled, preferably substantially constant, release of the 1,25-dihydroxyvitamin $D_2$ over an extended period of time. An optional but preferred method practiced with such a composition will ensure a substantially constant concentration of 1,25-dihydroxyvitamin $D_2$ in the body and a more sustained blood level. By providing a slow and steady release of the 1,25-dihydroxyvitamin $D_2$ over time, blood, intralumenal and intracellular Vitamin D concentration spikes, i.e., adverse supraphysiologic levels, are mitigated or eliminated. A gradual increase in, and then sustained blood levels of 1,25-dihydroxyvitamin $D_2$ is expected to provide dual unexpected benefits of unsurpassed effectiveness in restoring blood 1,25-dihydroxyvitamin $D_2$ to optimal levels, and unsurpassed safety relative to heretofore known oral formulations of active Vitamin D or analogs.

In one optional aspect, the controlled release oral formulation will also effectively resist disintegration in gastric juice, and further optionally will avoid substantial (e.g., >50%) release of the contained 1,25-dihydroxyvitamin $D_2$ until it reaches the small intestine, and more preferably the ileum of the small intestine of humans.

Once released into the lumen of the ileum the 1,25-dihydroxyvitamin $D_2$ is absorbed into the bloodstream. In such an embodiment, preferably the major portion of 1,25-dihydroxyvitamin $D_2$ is absorbed at a point beyond the duodenum and jejunum. These proximal portions of the small intestine can respond to high intralumenal levels of Vitamin D compounds and, in the process, can catabolize significant quantities of the 1,25-dihydroxyvitamin $D_2$. By delaying release until the ileum, the pharmaceutical composition can virtually eliminate first pass effects on the proximal intestine, and reduce unwanted catabolism. Further, transileal absorption of 1,25-dihydroxyvitamin $D_2$ can be increased with a formulation described herein, which can be designed to direct the absorbed 1,25-dihydroxyvitamin $D_2$ onto the serum vitamin D-binding protein (DBP) versus into chylomicrons. It is believed that 1,25-dihydroxyvitamin $D_2$ bound to DBP is more protected from hepatic catabolism. Significant catabolism of administered 1,25-dihydroxyvitamin $D_2$ prior to or after its absorption into the bloodstream significantly lowers its systemic bioavailability. Elimination of first pass effects reduces the risk of Vitamin D toxicity.

Thus, one embodiment of the invention is a method of administering an amount of 1,25-dihydroxyvitamin $D_2$ to a patient such that the maximum serum concentration of 1,25-dihydroxyvitamin D in a dose interval (Cmax) is reduced as compared to an equivalent amount of 1,25-dihydroxyvitamin $D_2$ administered by bolus IV injection and/or an equivalent immediate-release, oral dosage form. Similarly, the invention provides a controlled-release dosage form having a quantity of 1,25-dihydroxyvitamin $D_2$ that, when administered to a patient, results in a Cmax of 1,25-dihydroxyvitamin D less than an equivalent amount of 1,25-dihydroxyvitamin $D_2$ administered by bolus IV injection and/or by an equivalent immediate-release, oral dosage form. For example, the reduction is preferably by a factor of at least 50%, 60%, 7096, or 80%.

Another embodiment of the invention is a method of administering an amount of 1,25-dihydroxyvitamin to a patient such that the maximum change in serum concentration of 1,25-dihydroxyvitamin in a dose interval is reduced as compared to an equivalent amount of 1,25-dihydroxyvitamin $D_2$ administered by bolus IV injection and/or an equivalent immediate-release, oral dosage form. Similarly, the invention provides a controlled-release dosage form having a quantity of 1,25-dihydroxyvitamin $D_2$ that, when administered to a patient, results in a maximum change in serum concentration of 1,25-dihydroxyvitamin $D_2$ in a dose interval less than an equivalent amount of 1,25-dihydroxyvitamin $D_2$ administered by bolus IV injection and/or by an equivalent immediate-release, oral dosage form. For example, the reduction is preferably by a factor of at least 50%, 60%, 70%, or 80%.

Still another embodiment of the invention is a method of administering an amount of 1,25-dihydroxyvitamin $D_2$ to a patient such that the ratio of the maximum serum concentration after administration of 1,25-dihydroxyvitamin $ID_2$ to the concentration 24 hours after administration ($Cmax_{24hr}/C_{24hr}$) is reduced as compared to an equivalent amount of 1,25-dihydroxyvitamin $D_2$ administered by bolus IV injection and/ or an equivalent immediate-release, oral dosage form. Similarly, the invention provides a controlled-release dosage form having a quantity of 1,25-dihydroxyvitamin $D_2$ that, when administered to a patient, results in $Cmax_{24hr}/C_{24hr}$ of 1,25-dihydroxyvitamin $D_2$ less than an equivalent amount of 1,25-dihydroxyvitamin $D_2$ administered by bolus IV injection and/ or by an equivalent immediate-release, oral dosage form. For example, the reduction is preferably by a factor of at least 50%, 60%, 70%, or 80%.

Yet another embodiment of the invention is a method of administering an amount of 1,25-dihydroxyvitamin $D_2$ to a patient such that the elimination half-life ($t_{1/2}$) of 1,25-dihydroxyvitamin $D_2$ is increased as compared to an equivalent amount of 1,25-dihydroxyvitamin $D_2$ administered by bolus IV injection and/or an equivalent immediate-release, oral dosage form. Similarly, the invention provides a controlled-release dosage form having a quantity of 1,25-dihydroxyvitamin $D_2$ that, when administered to a patient, results in a $t_{1/2}$ of 1,25-dihydroxyvitamin $D_2$ greater than that of an equivalent amount of 1,25-dihydroxyvitamin $D_2$ administered by bolus IV injection and/or by an equivalent immediate-release, oral dosage form. For example, the increase is preferably by a factor of at least 25%, 30%, 40%, 50%, or 60%.

A further embodiment of the invention is a method of administering an amount of 1,25-dihydroxyvitamin $D_2$ to a patient such that the time for the plasma concentration of 1,25-dihydroxyvitamin $D_2$ to reach its maximum in a dose interval following administration (Tmax) is increased as compared to an equivalent amount of 1,25-dihydroxyvitamin $D_2$ administered by bolus IV injection and/or an equivalent immediate-release, oral dosage form. Similarly, the invention provides a controlled-release dosage form having a quantity of 1,25-dihydroxyvitamin $D_2$ that, when administered to a patient, results in a Tmax for 1,25-dihydroxyvitamin $D_2$ greater than that of an equivalent amount of 1,25-dihydroxyvitamin administered by bolus IV injection and/or by an equivalent immediate-release, oral dosage form. For example, the increase is preferably by a factor of at least 25%, 30%, 40%, 50%, or 60%.

In one embodiment of the invention, the controlled release oral formulation of 1,25-hydroxyvitamin $D_2$ is prepared generally according to the following procedure. A sufficient quantity of 1,25-hydroxyvitamin $D_2$ is completely dissolved in a minimal volume of USP-grade absolute ethanol (or other suitable solvent) and mixed with appropriate amounts and types of pharmaceutical-grade excipients to form a matrix which is solid or semi-solid at both room temperature and at the normal temperature of the human body, or a solvent mass which may be in a semi-solid or liquid form at room temperature and/or at body temperature. The matrix or solvent mass is completely, almost entirely, substantially, or partially resistant to digestion in the stomach and upper small intestine, and it gradually disintegrates in the lower small intestine.

In a suitable formulation, the matrix or solvent mass binds the 1,25-hydroxyvitamin $D_2$ and permits a slow, relatively steady, i.e. substantially constant, release of the 1,25-hydroxyvitamin $D_2$ over a period of four to eight hours or more, by simple diffusion and/or gradual disintegration, into the contents of the lumen of the lower small intestine. This preferred formulation further optionally has an enteric coating that partially dissolves in aqueous solutions having a pH of about 7.0 to 8.0, or simply dissolves slowly enough that significant release of 1,25-hydroxyvitamin $D_2$ is delayed until after the formulation passes through the duodenum and jejunum.

As discussed above, the means for providing the controlled release of 1,25-hydroxyvitamin $D_2$ may be selected from any of the known controlled release delivery systems of an active ingredient over a course of about four or more hours including the wax matrix system, and the Eudragit RS/RL system (of Rohm Pharma, GmbH, Weiterstadt, Germany).

The wax matrix system provides a lipophillic matrix. The wax matrix system may utilize, bees wax, white wax, cachalot wax or similar compositions. The active hormone is dispersed in the wax binder, which slowly disintegrates in intestinal fluids to gradually release the active ingredient. The wax binder that is impregnated with the 1,25-hydroxyvitamin is loaded into partially-crosslinked, soft gelatin capsules. The wax matrix system disperses the active ingredient in a wax binder which softens at body temperature and slowly disintegrates in intestinal fluids to gradually release the active ingredient. The system suitably includes a mixture of waxes, with the optional addition of oils, to achieve a melting point which is higher than body temperature and preferably lower than the melting temperature of gelatin formulations typically used to create the shells of either soft and/or hard gelatin capsules or other formulations used to create enteric coatings.

Specifically, in one suitable embodiment, the waxes selected for the matrix are melted and thoroughly mixed. The desired quantity of optional oils is added at this time, followed by sufficient mixing. The waxy mixture is then gradually cooled to a temperature just above its melting point. The desired amount of 1,25-hydroxyvitamin $D_2$, dissolved in ethanol, is uniformly distributed into the molten matrix, and the matrix is loaded into soft gelatin capsules. The filled capsules are treated for appropriate periods of time with a solution containing an aldehyde, such as acetaldehyde, to partially crosslink the gelatin in the capsule shell. The gelatin shell becomes increasingly crosslinked, over a period of several weeks and, thereby, more resistant to dissolution in the contents of stomach and upper intestine. When properly constructed, this gelatin shell will gradually dissolve after oral administration and become sufficiently porous (without fully disintegrating) by the time it reaches the ileum to allow the 1,25-hydroxyvitamin $D_2$ to diffuse slowly from the wax matrix into the contents of the lower small intestine.

Examples of other lipid matrices that may be of value are glycerides, fatty acids and alcohols, and fatty acid esters.

Thus, one type of particularly preferred controlled release formulation is a solid or semi-solid, waxy pharmaceutical formulation for controlled release of the vitamin D hormone in the gastrointestinal tract of a subject which ingests the formulation. The formulation includes a waxy controlled release carrier agent, a lipoidic agent, an oily vehicle for the vitamin D compound, and the vitamin D hormone 1,25-dihydroxyvitamin The formulation provides for controlled release of the vitamin D compound incorporated therein. The formulation is free of or essentially free of disintegrants.

The waxy controlled release carrier provides for a formulation which is solid or semi-solid at room temperature and solid, semi-solid, or liquid at body temperature, preferably semi-solid or liquid at body temperature. Examples of carriers suitable for use include waxes, such as synthetic wax, microcrystalline wax, paraffin wax, carnauba wax, and beeswax; polyethoxylated castor oil derivatives, hydrogenated vegetable oils, glyceryl mono-, di- or tribehenates; long-chain alcohols, such as stearyl alcohol, cetyl alcohol, and polyethylene glycol; and mixtures of any of the foregoing. Non-digestible waxy substances, such as hard paraffin wax, are preferred.

The waxy carrier preferably is present in an amount greater than about 5% of the formulation, based on the total weight of the formulation excluding any additional coatings or shells (wt %). For example, the waxy carrier can comprise greater than 5 wt % of the formulation, greater than 10 wt % of the formulation, greater than 15 wt % of the formulation, greater than 20 wt % of the formulation, and greater than 25 wt % of the formulation. The waxy carrier is preferably present in an amount less than 50 wt %, less than 40 wt %, less than 35 wt %, or less than 30 wt.%. Suitable ranges include 5 wt % to 35 wt %, 15 wt % to 35 wt % and 20 to 30 wt %. Examples include 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, and 30 wt %.

The lipoidic agent provides for release of the vitamin D compound from the formulation in the gastrointestinal tract of the subject being treated. Without intending to be bound by any particular theory of operation, it is believed that the lipoidic agent can serve one or more preferred functions such as creating a micro-emulsion of the oily vehicle in gastrointestinal fluid; providing prolonged gastric retention, for example by bioadhesive properties such that the formulation interacts with the mucous layer of the stomach; and in enhancing absorption of the vitamin D compound. However, regardless of the mechanism of action, the invention is not limited by any particular mode of operation.

The lipoidic agent components preferably are amphiphiles, in which the molecule or ion contains both hydrophilic and lipophilic portions. These components can be defined by a numerical value based on the Hydrophile/Lipophile Balance system ("HLB system"). The HLB scale is a numerical scale, extending from 0 to approximately 20, where lower numbers denote more lipophilic and hydrophobic substances, and higher numbers denote more hydrophilic and lipophobic substances. The affinity of a compound for water, or for oily substances, is determined and its HLB value is assigned experimentally. The FILB of the hydrophobic carrier employed herein preferably will be in a range of about 13 to about 18.

A variety of pharmaceutically acceptable lipoidic agents may be incorporated in the foi ululation. The quantity of lipoidic agent present in the formulation is preferably at least 5 wt %, at least 15 wt %, at least 35 wt %, at least 40 wt % or at least 45 wt %. Suitable ranges include about 5 wt % to about 60 wt %, about 20 wt % to about 60 wt % and about 40 wt % to about 50 wt %.

In one embodiment, the lipoidic agent is a lipophilic emulsifier which has an HLB of less than 7 and comprises a member selected from the group consisting of mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof.

A preferred lipoidic agent is selected from glycerides and derivatives thereof. Preferred glycerides are selected from the group consisting of medium or long chain glycerides, caprylocaproyl macrogolglycerides, and mixtures thereof.

Preferred medium chain glycerides include, but are not limited to, medium chain monoglycerides, medium chain diglycerides, caprylic/capric triglyceride, glyceryl monolaurate, glyceryl monostearate, caprylic/capric glycerides, glycerylmonocaprylate, glyceryl monodicaprylate, caprylic/capric linoleic triglyceride, and caprylic/capric/succinic triglyceride.

Monoglycerides having a low melting point are preferred for making the formulation, and are easily soluble in the intestines. Preferred monoglycerides include but are not limited to, glyceryl monostearate, glyceryl monopalmitate, glyceryl monooleate, glyceryl monocaprylate, glyceryl monocaprate, glyceryl monolaurate, etc., preferably glyceryl monostearate (GMS). GMS is a natural emulsifying agent. It is oil soluble, but poorly soluble in water. GMS has an HLB value of 3.8. Another preferred monoglyceride is glyceryl monooleate (GMO). GMO is also a natural emulsifying agent; it is oil soluble, but poorly soluble in water, and it has an HLB value of 3.8.

In another embodiment, the glyceride is an absorption enhancer selected from caprylocaproyl macrogolglycerides. Caprylocaproyl macrogolglycerides which may be employed include, but are not limited to, polyethylene glycosylated glycerides, also known as polyglycolized glycerides or PEGylated glycerides. PEGylated glycerides which may be employed in the composition include, but are not limited to, mixtures of monoglycerides, diglycerides, and triglycerides and monoesters and diesters of polyethylene glycol, polyethylene glycosylated almond glycerides, polyethylene glycosylated corn glycerides, and polyethylene glycosylated caprylic/capric triglyceride. The absorption enhancer preferably has an HLB value from 13 to 18, more preferably from 13 to 15.

One preferred absorption enhancer is known under the trade name GELUCIRE, and is commercially available from Gattefossé Corporation, Paramus, N.J., USA. GELUCIRE is a well known excipient which is a family of fatty acid esters of glycerol and PEG esters, also known as polyglycolized glycerides. GELUCIRE is used in various applications including preparing sustained release pharmaceutical compositions. GELUCIRE compounds are inert, semi-solid waxy materials which are amphiphilic and are available with varying physical characteristics such as melting point, HLB, and solubilities in various solvents. They are surface active in nature and disperse or solubilize in aqueous media forming micelles, microscopic globules or vesicles. They are identified by their melting point/HLB value. The melting point is expressed in degrees Celsius. One or a mixture of different grades of GELUCIRE excipient may be chosen to achieve the desired characteristics of melting point and/or HLB value. The preferred GELUCIRE composition is GELUCIRE 44/14, a semisolid waxy material with a melting point of 44° C. and a HLB of 14.

Another preferred polyglycolyzed glyceride absorption enhancer is caprylocaproyl macrogol-8-glyceride (CAS No. 85536-07-8 and 84963-88-2). This is a mixture of mono-, di- and triesters of glycerol and of PEG 400 with medium-chain fatty acids ($C_8$-$C_{10}$) which is marketed, for example, by Gattefosse Corporation, Paramus, N.J., USA under the trade name LABRASOL. LABRASOL has a HLB value of 14 and has the following composition by weight: $C_8$-$C_{10}$ monoglycerides approximately 4%; $C_8$-$C_{10}$ diglycerides approximately 17%; $C_8$-$C_{10}$ triglycerides approximately 6%; $C_8$-$C_{10}$ monoesters of PEG 400 approximately 14%; $C_8$-$C_{10}$ diesters of PEG 400 approximately 36%; free PEG 400 approximately 20%; free glycerol approximately 3%.

Preferably, the lipoidic agent includes a mixture of a lipophilic emulsifier which has an HLB of less than 7 and an absorption enhancer that preferably has an HLB value from 13 to 18. The lipophilic emulsifier is preferably present in an amount in a range of about 20 wt % to about 50 wt %, preferably about 30 wt % to about 40 wt %, and the absorption enhancer is preferably present in an amount of about 5 to about 20 wt %, preferably about 8 to about 15 wt %.

The low melting points of many of the solid lipoidic compositions provide a means of incorporating the pharmaceutically active ingredients in them at temperatures from about 0° C. to about 50° C. above their respective melting points, and then filling the melt (solution and/or dispersion) in animal or vegetable gelatin capsules. The melt solidifies inside the capsules upon cooling to room temperature.

The oily component serves as a vehicle, preferably the main vehicle, for the vitamin D compound. Any pharmaceutically-acceptable oil can be used. Examples include animal (e.g., fish), vegetable (e.g., soybean), and mineral oils. The oil preferably will readily dissolve the vitamin D compound used. Preferred oily components include non-digestible oils, such as mineral oils, particularly liquid paraffins, and squalene. The oil vehicle preferably comprises about 10 wt % to about 50 wt % of the formulation, more preferably about 15 wt % to about 45 wt % about 20 wt % to about 40 wt %, or about 15 wt % to about 25 wt %. In one preferred embodiment, the liquid paraffin can be characterized by one or more of the following parameters: specific gravity about 0.88 to 0.89; kinematic viscosity (40° C.) abut 64 to about 70 cSt; molecular weight 424; % paraffinic hydrocarbons about 59; and pour point −24° C. The ratio between the waxy component and the oily component can be optimized in order to achieve the desired rate of release of the vitamin D compound. Thus, if a heavier oil component is used, relatively less of the waxy component can be used, and if a lighter oil component is used, then relatively more waxy component can be used.

Another suitable controlled-release oral drug delivery system is the Eudragit RL/RS system in which the active ingredient 1,25-hydroxyvitamin $D_2$ is formed into granules having a dimension of 25/30 mesh. The granules are then uniformly coated with a thin polymeric lacquer which is water insoluble but slowly water permeable. The coated granules can be mixed with optional additives such as antioxidants, stabilizers, binders, lubricants, processing aids and the like. The mixture may be compacted into a tablet which, prior to use, is hard and dry and can be further coated, or it may be poured into a capsule. After the tablet or capsule is swallowed and comes into contact with the aqueous intestinal fluids, the thin lacquer begins to swell and slowly allows permeation by intestinal fluids. As the intestinal fluid slowly permeates the lacquer coating, the contained 1,25-hydroxyvitamin $D_2$ is slowly released. By the time the tablet or capsule has passed through the small intestine, about four to eight hours or more later, the 1,25-hydroxyvitamin $D_2$ will have been gradually but completely released. Accordingly, the ingested tablet will release a stream of 1,25-hydroxyvitamin $D_2$ as well as any other optional active ingredient.

The Eudragit system is comprised of high permeability lacquers (RL) and low permeability lacquers (RS). RS is a water insoluble film former based on neutral swellable methacrylic acids esters with a small proportion of trimethylammonioethyl methacrylate chlorides, and the molar ratio of the quaternary ammonium groups to the neural ester group is about 1:40. RL is also a water insoluble swellable film former based on neutral methacrylic acid esters with a small portion of trimethylammonioethyl methacrylate chloride, and the molar ratio of quateranary ammonium groups to neutral ester groups is about 1:20. The permeability of the coating and thus the time course of drug release can be titrated by varying the proportion of RS to RL coating material. For further details of the Eudragit RL/RS system, reference is made to technical publications available from Rohm Tech, Inc. 195 Canal Street, Maiden, Mass., 02146. See also, K. Lehmann, D. Dreher "Coating of tablets and small particles with acrylic resins by fluid bed technology", Int. J. Pharm. Tech. & Prod. Mfr. 2(r), 31-43 (1981), incorporated herein by reference.

Other examples of insoluble polymers include polyvinyl esters, polyvinyl acetals, polyacrylic acid esters, butadiene styrene copolymers and the like.

Once the coated granules or other formulations are either formed into a tablet or put into a capsule, the tablet or capsule is optionally coated with an enteric-coating material which dissolves at a pH of 7.0 to 8.0. One such pH-dependent enteric-coating material is Eudragit L/S which dissolves in intestinal fluid but not in the gastric juices. Other enteric coating materials may be used, such as cellulose acetate phthalate (CAP) which is resistant to dissolution by gastric juices but readily disintegrates due to the hydrolytic effect of the intestinal esterases.

The particular choice of enteric-coating material and/or controlled release material will delay substantial release of the 1,25-hydroxyvitamin $D_2$, for example until the formulation reaches the ileum. The particular choice of controlled release method and material (e.g., coating, matrix, or other medium) will preferably provide a substantially constant release of the 1,25-hydroxyvitamin $D_2$ over a period of 4 to 8 hours or more.

In one preferred class of embodiments, the modified release formulation releases at least 70%, more preferably at least 80% of the vitamin D compound within the first 24 hours after dosing, for example about 72%.

Administration of 1,25-dihydroxyvitamin $D_2$ as described herein also allows for the efficient and predictable delivery of a predetermined dosage of vitamin D hormone to a patient. The temporal and quantitative availability of the active vitamin $D_2$ hormone is not dependent on activation in the liver or other metabolism. Accordingly, lower dosages, compared to other vitamin $D_2$ analogs, are considered possible in order to achieve equivalent effects, while optionally or preferably avoiding or reducing side effects, as described above.

As described herein, oral and intravenous dosage formulations and routes are preferred. The administration of such therapies can be on an episodic basis, suitably from daily, 6, 5, 4, 3, 2, or 1 times a week.

In embodiments, the method is contemplated to include administering a formulation described herein to raise and preferably also maintain blood 1,25-dihydroxyvitamin $D_2$ levels at 25 pg/mL, 30 pg/mL, or higher, e.g. 25-65 pg/mL for an extended period, for example at least one month, at least three months, at least six months, or longer.

The dosage of the 1,25-dihydroxyvitamin $D_2$ for oral or parenteral administration generally is about 0.1 μg per week to 100 μg per week, preferably about 0.7 μg per week to about 70 μg per week, which can be split into daily or other periodic doses, such as three times per week for administration concomitant with hemodialysis. In exemplary embodiments, a parenteral dosage equivalent to about 0.5 μg per day to about 2 μg per day is contemplated, while an oral dosage equivalent to about 0.1, 0.5, 1, 2, 3, 4, 5, 6, 7, 8, 9, or 10 μg per day is contemplated.

Generally, the 1,25-dihydroxyvitamin $D_2$ is dispensed by unit dosage form comprising about 0.1 μg to about 10 μg in a pharmaceutically acceptable carrier per unit dosage, for example about 1 μg to about 4 μ. A sustained-release or delayed, sustained-release unit dosage form including about 2 μg to about 10 μg, or about 3 μg to about 5 μg is also contemplated.

The formulation can be prepared by procedures well known to one of ordinary skill in the art. Typically, the pharmaceutically acceptable waxes, lipoidic agents, and oils are melted, if necessary, to provide a flowable liquid thereby making it easier to obtain a homogeneous mixture. The Vitamin D compound is added to the thus liquid carrier, for example dissolved in an alcohol such as anhydrous ethanol, and the ingredients are mixed to provide a homogeneous mixture. The mixture can be cooled and stored prior to later division into unit dosage forms, such as filled gelatin capsules.

In one preferred method, a portion of the oil vehicle, solid wax, and a lipophilic emulsifier are heated to a relatively high temperature (e.g., 65° C.) and mixed prior to adding an absorption enhancer, followed by additional mixing until homogenous, then cooling to an intermediate elevated temperature (e.g., 50° C. to 55° C.). In a separate vessel, an antioxidant preservative and the remainder of the oil vehicle are mixed and heated to an intermediate elevated temperature 50° C.), then combined and mixed with the wax mixture until a homogenous solution is obtained. Next, a solution of vitamin D compound in alcohol is combined with the homogenous waxy solution, mixed until a homogenous solution is obtained, preferably filled into capsules, and then cooled to room temperature. In another preferred method, a portion of the oil vehicle, solid wax, and a lipophilic emulsifier are heated at a temperature of 55° C. to 60° C. and mixed prior to adding an absorption enhancer, followed by additional mixing until homogenous. In a separate vessel, an antioxidant preservative and the remainder of the oil vehicle are mixed and heated to a temperature of 55° C. to 60° C., then combined and mixed with the wax mixture until a homogenous solution is obtained. Next, a solution of vitamin D compound in alcohol is combined with the homogenous waxy solution, mixed until a homogenous solution is obtained, preferably filled into capsules, and then cooled to room temperature.

The formulation preferably is placed in capsules prior to administration to the patient in need of treatment. Such capsules may be hard or soft, and soft capsules are preferred. The formulation may be filled into gelatin capsules using standard capsule filling machinery, such as by melting the formulation and injection filling it into soft capsule shells.

The formulation and methods of use and making are contemplated to include embodiments including any combination of one or more of the additional optional elements, features, and steps further described below, unless stated otherwise.

Thus, in one type of embodiment, the formulation further includes a preservative, such as an antioxidant. Butylated hydroxytoluene (BHT) is preferred.

In another type of embodiment, the vitamin D compound is administered in combination with one or more other therapeutic agents.

As described above, the formulation is preferably filled into gelatin capsules, but it may also be administered in neat form, or with one or more external coating layers, such as an enteric coating. It is also contemplated that the formulation can be pressed into tablets, and in such cases one or more tablet pressing excipients may be included.

In the compositions and methods described herein, preferred steps, preferred components, preferred compositional ranges thereof, and preferred combinations of the foregoing, can be selected from the various specific examples provided herein. For example, a preferred formulation includes a therapeutically effective amount of 1,25-hydroxyvitamin $D_2$, about 2 wt % (e.g., 2.32 wt %) ethanol, about 10 wt % (e.g., 9.75 wt %) GELUCIRE 44/14, about 27 wt % (e.g., 27.51 wt.%) hard paraffin, about 38 wt % (e.g., 37.85 wt %) GMS, about 22 wt % (e.g., 22.43 wt %) mineral oil, and optionally a small amount of preservative (e.g., 0.02 wt % BHT). A variation on this formulation will include about 20% hard paraffin and about 29% mineral oil.

Specifications for still another preferred embodiment of a base capsule fill formulation embodiment, are shown in Table 1 below.

TABLE 1

| Ingredient | % w/w |
|---|---|
| 1,25-hydroxyvitamin $D_2$ | effective amount |
| Dehydrated ethanol | 2.5 |
| Hard Paraffin | 20 |
| Mineral Oil | 30 |
| GELUCIRE 44/14 | 10 |
| GMS | 38 |
| BHT | 0.020 |

The dosages described herein are contemplated for any of the therapeutic methods described herein. It will be appreciated that the actual preferred amount of hormone in a specific case will vary according the particular compositions formulated, the mode of application, and the particular situs being treated. Dosages can be determined using conventional considerations, e.g., by customary comparison of the differential activity of the hormone and of a known agent, e.g. by means of an appropriate conventional pharmacological protocol.

The specific doses for each particular patient can depend on a wide variety of factors, for example, on the age, body weight, general state of health, sex, on the diet, on the timing and mode of administration, on the rate of excretion, and on medicaments used in combination and the severity of the particular disorder to which the therapy is applied.

Patients in need of vitamin D supplementation include healthy subjects and subjects at risk for vitamin D insufficiency or deficiency, for example, subjects with Stage 1, 2, 3, 4 or 5 chronic kidney disease; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with a Sun Protection Factor (SPF) value of 8 reduces production of vitamin D by 95%, and higher SPF values may further reduce vitamin D); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis; and/or postmenopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D. Optionally excluded from the methods of the invention are therapeutic treatment of subjects suffering from renal osteodystrophy (including osteomalacia and osteitis fibrosa cystica).

In other aspects, the compositions and methods of the invention are useful for prophylactic or therapeutic treatment of vitamin D-responsive diseases, i.e., diseases where active vitamin D prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25-dihydroxyvitamin $D_2$ has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease. Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease, polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

Diseases which can benefit from a modulation in the levels of 1,25-dihydroxyvitamin $D_2$ or its analogs, include, but are not limited to: (i) in the parathyroid—hypo-parathyroidism, Pseudohypoparathyroidism, secondary hyperparathyroidism; (ii) in the pancreas—diabetes; (iii) in the thyroid—medullary carcinoma; (iv) in the skin—psoriasis; wound healing; (v) in the lung—sarcoidosis and tuberculosis; (vi) in the kidney—chronic kidney disease, hypophosphatemic VDRR, vitamin D dependent rickets; (vii) in the bone—anticonvulsant treatment, fibrogenisis imperfecta ossium, osteitis fibrosa cystica, osteomalacia, osteoporosis, osteopenia, osteosclerosis, renal osteodytrophy, rickets; (viii) in the intestine—glucocorticoid antagonism, idopathic hypercalcemia, malabsorption syndrome, steatorrhea, tropical sprue; and (ix) autoimmune disorders.

In embodiments of the invention, the disease that benefits from a modulation in the levels of 1,25-dihydroxyvitamin $D_2$, or an analog thereof, are selected from cancer, dermatological disorders (for example psoriasis), parathyroid disorders (for example hyperparathyroidism and secondary hyperparathyroidism), bone disorders (for example osteoporosis) and autoimmune disorders.

The methods and compositions described herein are particularly useful for treating abnormally elevated blood levels of PTH. The invention provides a method for treating or preventing hyperparathyroidism, such as secondary hyperparathyroidism, by lowering (or maintaining low) serum parathyroid hormone levels in a patient suffering from the disease. The method at the same time can ameliorate bone metabolism abnormalities which can develop in such patients.

Secondary hyperparathyroidism is a common complication of chronic kidney disease and thus a particular patient group contemplated is one with CKD. Patients at Stage 3, 4 and/or 5 CKD may be treated according to the present invention. Secondary hyperparathyroidism can also develop in individuals with healthy kidneys, due to environmental, cultural or dietary factors which prevent adequate vitamin D supply.

The methods described herein also intended to be used in the treatment or prevention of conditions in humans including, but not limited to: bone depletive disorders which respond to administration of active forms of vitamin D; immunoresponsive disorders which respond to administration of active forms of vitamin D; high blood pressure; bacterial infection; and cardiovascular disease.

EXAMPLES

The following examples are provided for illustration and are not intended to limit the scope of the invention.

Example 1

1,25-Dihydroxyvitamin $D_2$ for Treating Subjects with Low Serum 1,25-Dihydroxyvitamin D 1,25-dihydroxyvitamin $D_2$ is used as a treatment for subjects with low serum 1,25-dihydroxyvitamin D in a study involving 50 adults, ages 18-85 years.

The subjects have serum 1,25-dihydroxyvitamin D levels below 20 pg/dL and complete an eight-week baseline period and then 24 weeks of therapy with orally administered 1,25-dihydroxyvitamin $D_2$.

The initial dose of 1,25-dihydroxyvitamin $D_2$ is 1.0 μg, with increases in steps of 0.5 μg/day permitted after four weeks. The maximum dosage is limited to 5.0 μg/day of 1,25-dihydroxyvitamin $D_2$. Subjects are monitored at regular intervals for plasma iPTH, serum calcium and phosphorus, 24-hour and fasting urinary calcium, bone-specific serum markers, plasma total 1,25-dihydroxyvitamin $D_2$ and routine blood chemistries and hematologies.

After the 24 week treatment period the subjects treated with 1,25-dihydroxyvitamin $D_2$ show average serum phosphorous levels between about 2.5 and 4.5 mg/dL, average corrected serum calcium levels between about 8.6 and 10.2 mg/dL, average intact serum parathyroid hormone levels between about 65 pg/mL and 110 pg/mL, and average blood concentrations of 1,25-dihydroxyvitamin D between about 20 pg/mL and 60 pg/mL. Testing of serum 1,25-dihydroxyvitamin D levels between doses of 1,25-dihydroxyvitamin $D_2$ shows that serum 1,25-dihydroxyvitamin D levels in the patients are within the patients' normal historical physiological range for 1,25-dihydroxyvitamin D. Levels of serum bone-specific markers alkaline phosphatase, N- and C-telopeptides, and osteocalcin in patients show average normal levels of these markers.

Example 2

Double-Blind Study in End Stage Renal Disease (ESRD) Patients Exhibiting Secondary Hyperparathyroidism Up to 100 ESRD (End Stage Renal Disease) human patients undergoing chronic hemodialysis are studied in a multicenter, double-blind, placebo-controlled study. The selected patients reside in two major metropolitan areas within the continental U.S., have ages between 20 and 75 years, and have a history of secondary hyperparathyroidism. They have been on hemodialysis for at least four months, have a normal (or near normal) serum albumin, and have controlled serum phosphorus (often by using oral calcium phosphate binders).

On admission to the study, each patient is assigned at random to one of two treatment groups. One of these groups receives two consecutive 12-week courses of therapy with 1,25-dihydroxyvitamin $D_2$; the other group receives one 12-week course of therapy with 1,25-dihydroxyvitamin $D_2$ without interruption, by one 12-week course of placebo therapy. Each patient discontinues any 1α,25-dihydroxyvitamin $D_3$ therapy for eight weeks prior to initiating 1,25-dihydroxyvitamin $D_2$ therapy. Throughout this eight-week washout (or control) period and the two subsequent 12-week treatment periods, patients are monitored weekly for serum calcium and phosphorus. Serum intact PTH is monitored weekly or biweekly, and bone-specific serum markers, serum vitamin D metabolites, serum albumin, blood chemistries, hemoglobin and hematocrit are monitored at selected intervals.

During the study, patients undergo routine hemodialysis (three times per week) using a 1.24 mM calcium dialysate and ingest calcium phosphate binders (such as calcium carbonate or calcium acetate) in an amount sufficient to keep serum phosphate maintained in a range of 3.5 to 5.5 mg/dL. Patients who develop persistent mild hypercalcemia or mild hyperphosphatemia during the treatment periods reduce their 1,25-dihydroxyvitamin $D_2$ dosage. Patients who develop marked hypercalcemia (serum levels of total corrected calcium exceeds 10.2 mg/dL) or marked hyperphosphatemia (serum levels of phosphorus exceeds 5.5 mg/dL) immediately suspend treatment. Such patients are monitored at twice-weekly intervals until the serum calcium or phosphorus is normalized, and resume 1,25-dihydroxyvitamin $D_2$ dosing.

During the eight-week washout period, the mean serum level of PTH increases progressively and significantly. After initiation of 1,25-dihydroxyvitamin $D_2$ dosing, mean serum PTH decreases significantly to less than 50% of pretreatment levels. Due to this drop in serum PTH, some patients need to reduce their dosage of 1,25-dihydroxyvitamin $D_2$ to prevent excessive suppression of serum PTH. In such patients, exhibiting excessive suppression of serum PTH, transient mild hypercalcemia is observed, which is corrected by appropriate reductions in 1,25-dihydroxyvitamin $D_2$ dosages.

At the end of the first 12-week treatment period, mean serum PTH is in the desired range of 150 pg/mL to 300 pg/mL and serum levels of calcium and phosphorus are normal or near normal for end stage renal disease patients. At the end of the second 12-week treatment period (during which time 1,25-dihydroxyvitamin D₂ treatment is suspended and replaced by placebo therapy in one group), mean serum PTH values markedly increase, reaching pretreatment levels in the group receiving placebo therapy. Mean serum PTH remained controlled in the active group with serum levels of calcium and phosphorus remained normal of near normal. This study can demonstrate that 1,25-dihydroxyvitamin D₂ is effective in reducing serum PTH levels, and is safer than currently used therapies.

Example 3

Administration of Calcitriol and 1,25-dihydroxyvitamin D₂ to Rats

Sprague Dawley rats were given diet containing 0.75% adenine demonstrated previously to induce kidney failure [Levi et al., J. Amer. Soc. Neph., 17; 107-112]. After 4 weeks, normal diet was given to all animals. A control group receiving normal diet during the entire course of the study was used as normal control animals. After the 4 weeks of adenine diet treatment, animals were dosed i.v. 3×/week for 2 or 8 weeks with calcitriol or 1,25-dihydroxyvitamin D₂ at 0.01, 0.05, 0.1, 0.25 and 0.5 mg/kg. Serum, plasma kidney and parathyroid gland were collected after 2 and 8 weeks. iPTH and FGF23 in plasma and serum, respectively, were measured using a commercial Elisa kit. Serum calcium was measured using an ORTHO-CLINICAL VITROS 250 chemistry system or an o-cresolphthalein complexone-based assay. Serum phosphorus was measured using an ORTHO-CLINICAL VITROS 250 chemistry system or an ammonium molybdate-based assay. Fibronectin 1 was measured by real-time PCR from cDNA isolated from kidney.

FIG. 1 shows measured iPTH levels in adenine treated animals after two weeks of dosing with either 1,25-dihydroxyvitamin D₂, 1,25-dihydroxyvitamin D₃, or vehicle. For reference, PTH values are also shown for animals in the study fed a normal diet (without adenine). Both 1,25-dihydroxyvitamin D₂ and 1,25-dihydroxyvitamin D₃ in a dose dependant manner can suppress serum PTH levels. The levels of suppression for the doses shown are not significantly different between the two compounds. These results suggest that these compounds are essentially equivalent with respect to their efficacy in inhibiting the expression of PTH.

FIG. 2 shows measured serum calcium levels for calcitriol-treated animals, and FIG. 3 shows measured serum calcium levels for 1,25-dihydroxyvitamin D₂-treated animals. Calcitriol-treated animals showed a significant elevation of calcium at doses greater than 0.10 μg/kg, whereas 1,25-dihydroxyvitamin D₂-treated animals showed significance at doses greater than 0.05 μg/kg. A calcitriol dose of 0.10 μg/kg corresponded to about 13.6% PTH inhibition, whereas a 1,25-dihydroxyvitamin D₂ dose of 0.05 μg/kg corresponded to about 82.7% PTH inhibition. These findings indicate that L25-dihydroxyvitamin D₂ appears to be less likely to cause calcemia than 1,25-dihydroxyvitamin D₃ at doses that have equivalent efficacy.

Figure 5:
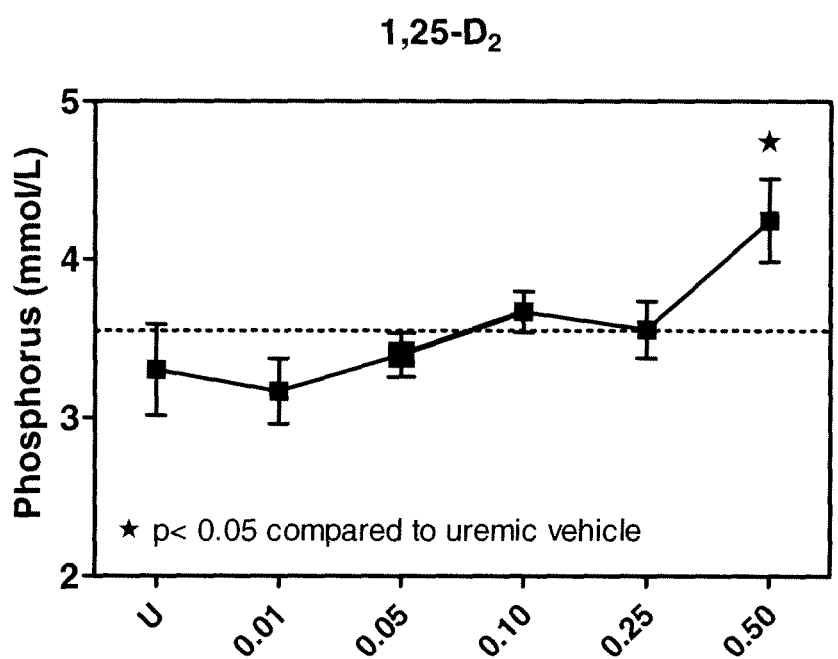
FIG. 5 shows measured serum phosphorous levels for 1,25-dihydroxyvitamin $D_2$-treated animals, according to Example 3.

FIG. 4 shows measured serum phosphorous levels for calcitriol-treated animals, and FIG. 5 shows measured serum phosphorous levels for 1,25-dihydroxyvitamin D₂-treated animals. Calcitriol-treated animals showed a significant elevation of phosphorous at the two highest doses, whereas 1,25-dihydroxyvitamin D₂-treated animals showed significance only at the highest dose.

Figure 6:
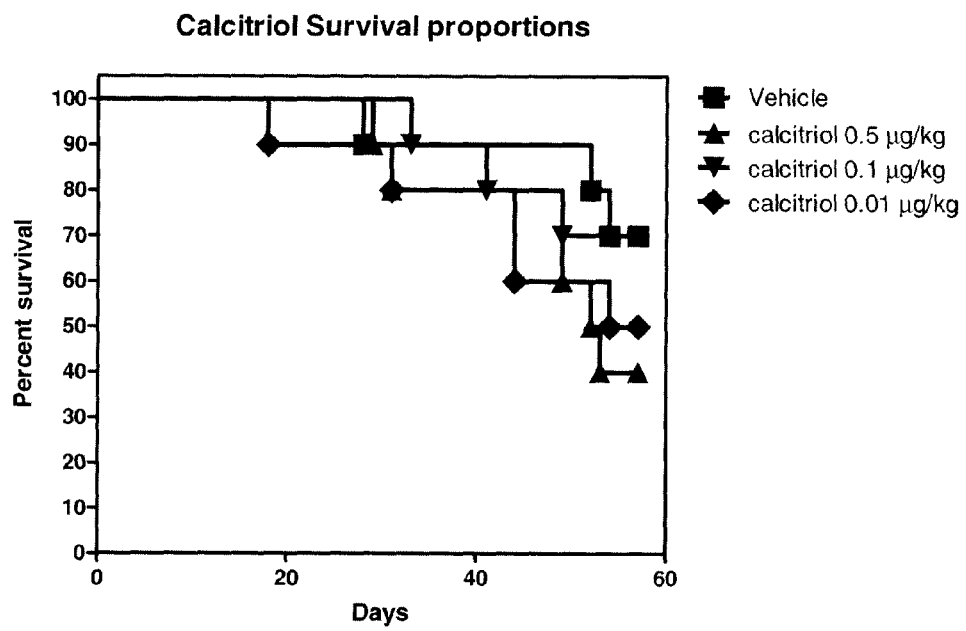
FIG. 6 shows survival data for calcitriol-treated animals.
Figure 7:
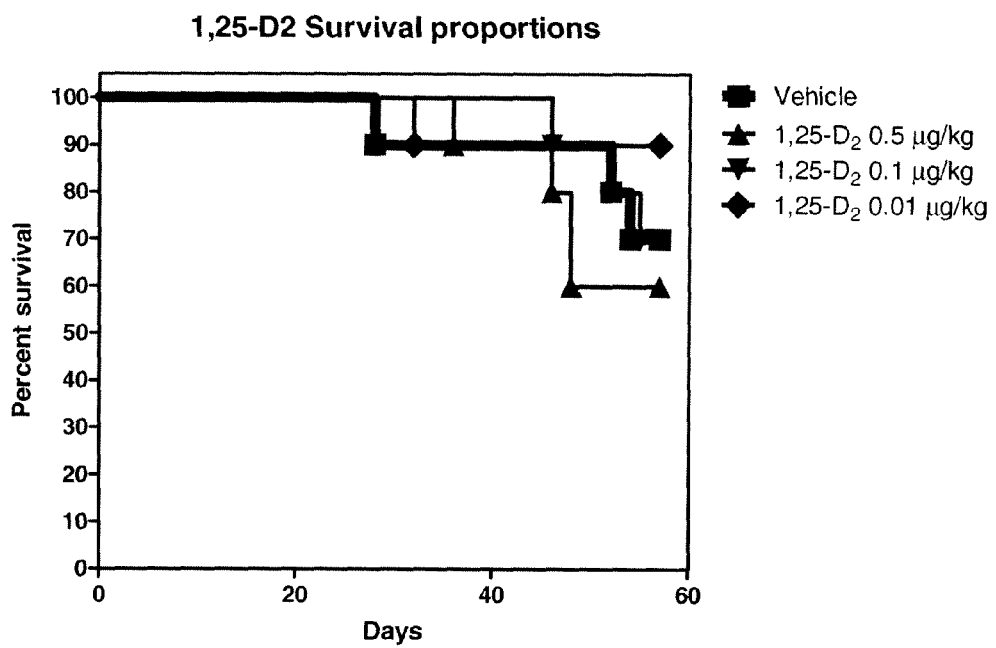
FIG. 7 shows survival data for 1,25-dihydroxyvitamin $D_2$-treated animals, according to Example 3.

FIG. 6 shows survival data for calcitriol-treated animals, and FIG. 7 shows survival data for 1,25-dihydroxyvitamin D₂-treated animals in a prospective study.

Figure 8:
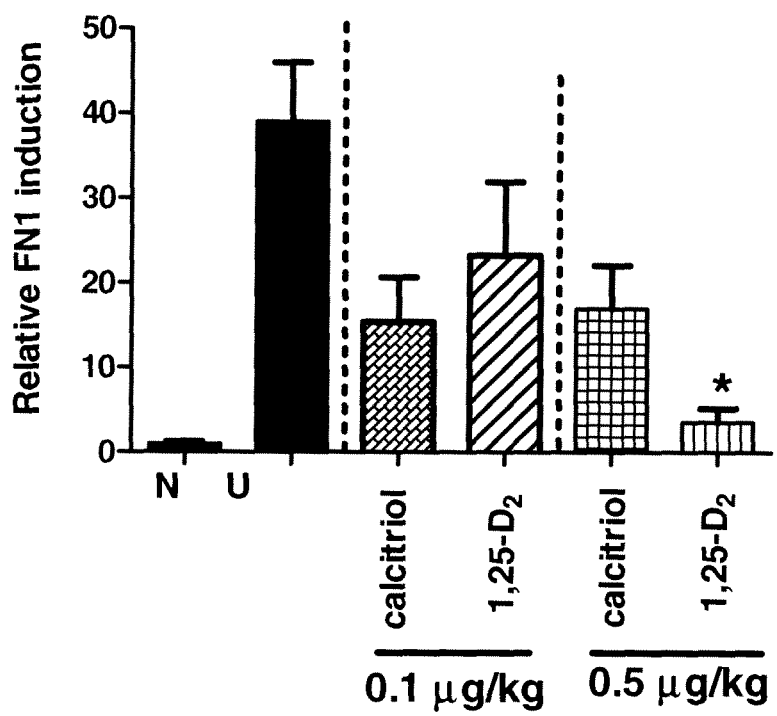
FIG. 8 shows relative renal FN1 induction in control, calcitriol, and 1,25-dihydroxyvitamin $D_2$-treated rats having adenine-induced kidney failure according to Example 3.

FIG. 8 shows relative renal FN1 induction after 12 days of treatment. The extent of suppression of renal FN1 expression observed at 0.5 mg/kg was significantly greater for 1,25-dihydroxyvitamin D₂-treated animals compared to calcitriol-treated animals. No difference in suppression between the two compounds was observed at 0.1 mg/kg.

Example 4

Stability of Compounds in Human Intestine

Equal parts of 0.1 M phosphate buffer (pH 7.4), NADPH, G-6-P, and G-6-P dehydrogenase were mixed to create a NADPH-generating system, and the final concentration of NADPH, G-6-P, and G-6-P dehydrogenase were 0.8 mM, 8 mM and 0.8 U/ml.

1,25-dihydroxyvitamin D₂ and calcitriol were added in to the NADPH-generating system. The final concentrations of the two vitamin D compounds were each 3.3 mM. A reaction was initiated by the addition of the human intestine microsomes (22 mg/ml) after a 5 min pre-incubation of the reaction at 37° C. After incubation for 60 min, the reaction was terminated by addition of cold 100% acetonitrile. An aliquot of the samples was injected into HPLC to determine the % remaining of the compound.

Figure 9:
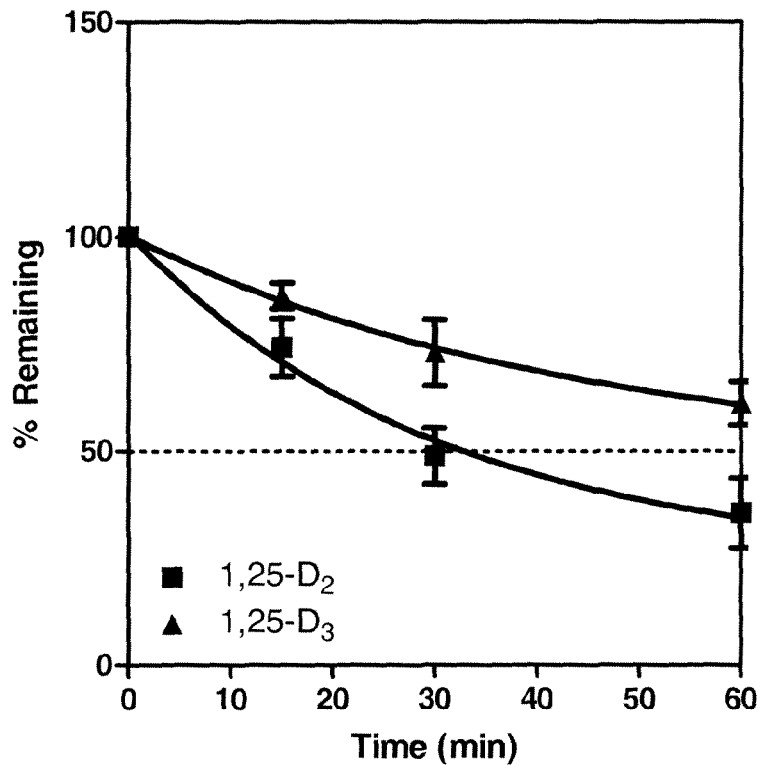
FIG. 9 shows % calcitriol and 1,25-dihydroxyvitamin $D_2$ remaining after incubation with human intestine microsomes according to Example 4.

Results are shown in FIG. 9, and demonstrate that 1,25-dihydroxyvitamin D₂ is metabolically unstable in human intestinal epithelia. Selective instability in intestine is an advantage in vitamin D therapy and may be a factor in accounting for reduced toxicity of 1,25-dihydroxyvitamin D₂.

Example 5

Alkaline Phosphatase and CYP24 Activity in C2BBe1 Cells

C2BBe1 cells were treated with 1 mM, 100 nM, and 10 nM 1,25-dihydroxyvitamin D₂ and calcitriol. Cells were incubated for 8 hours at 37° C. The cells were then lysed in 1 ml of TRIzol reagent. RNA was isolated from cell lysates through phase separation, as per the manufacturer's instructions (INVITROGEN). After cDNA synthesis, real-time PCR was used to quantify alkaline phosphatase and CYP24.

Figure 10:
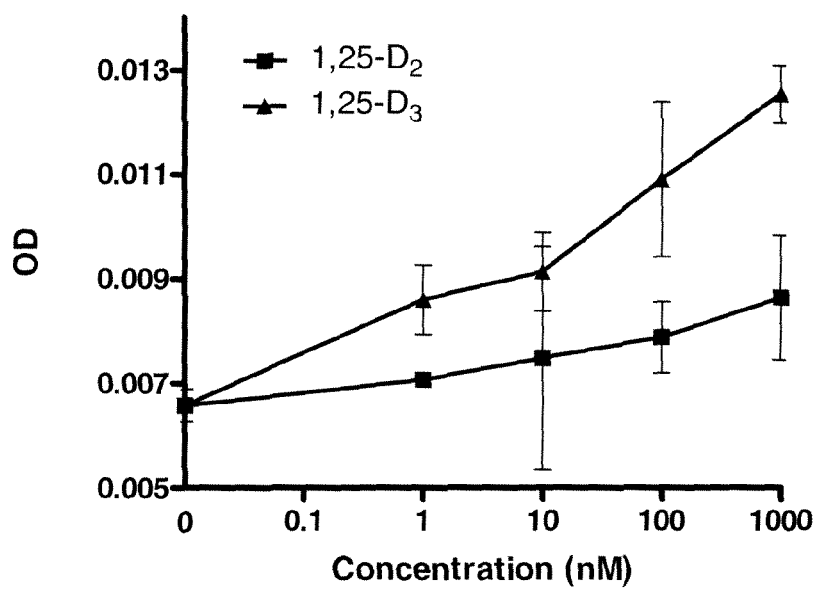
FIG. 10 and FIG. 11 show measured alkaline phosphatase and CYP24 activity in C2BBe1 cells, respectively, after incubation with calcitriol and 1,25-dihydroxyvitamin $D_2$ according to Example 5.
Figure 11:
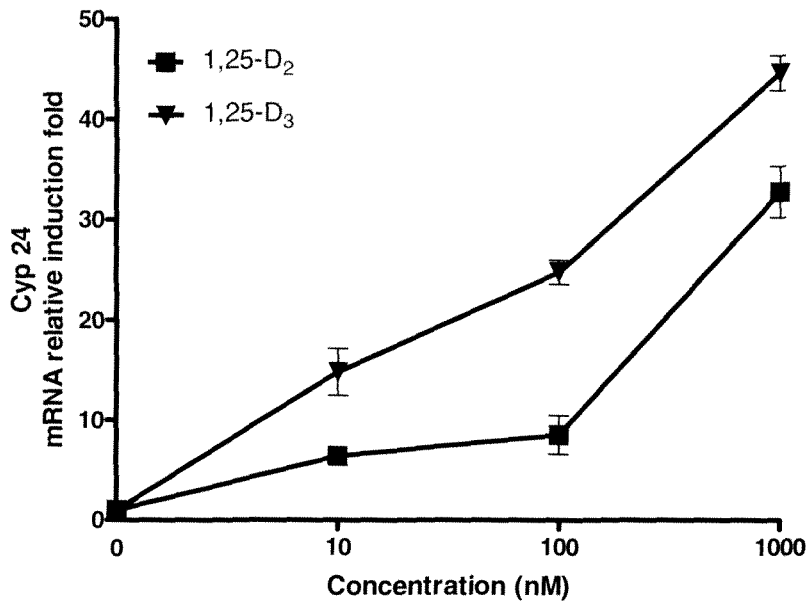

Measured alkaline phosphatase and CYP24 activity are shown in FIG. 10 and FIG. 11, respectively, and demonstrate that 1,25-dihydroxyvitamin D₂ is not a potent inducer of IAP activity. Furthermore, the similarity between IAP and CYP24 responses suggests metabolic differences in these cells.

Example 6

Intestinal Alkaline Phosphatase IAP Induction in Caco-2 Cells

Figure 12:
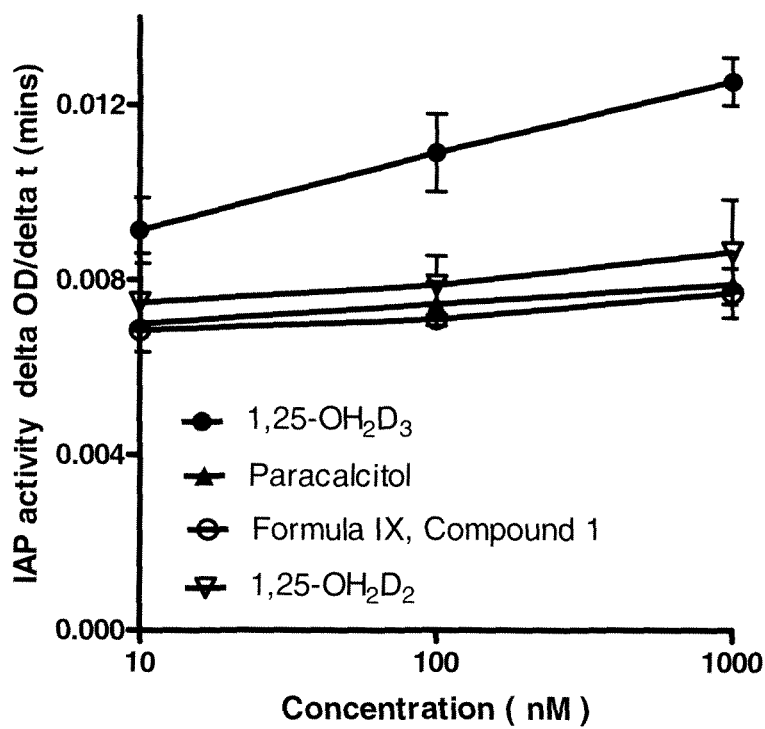
FIG. 12 shows the intestinal alkaline phosphatase IAP activity in Caco-2 cells, after incubation with calcitriol 1,25-dihydroxyvitamin $D_2$, and vitamin D analogs, according to Example 6.

FIG. 12 shows the intestinal alkaline phosphatase IAP activity in Caco-2 cells (change in mRNA optical density per change in unit time) following treatment with calcitriol (top line), 1,25-dihydroxyvitamin D₂ (next set of data and line down), 19-nor, 1,25-dihydroxyvitamin D₂ (paricalcitol, next set of data and line down), and an active vitamin D hormone analog which is disclosed as Formula IX (Compound 1) in U.S. Pat. No. 6,380,408 (col. 6), which is (5Z,7E,16Z,23E)-(1S,3R)-25-nor-25-t-butylsulfonyl-9,10-seco-5,7,10(19),16,23-cholestapentaene-1,3-diol (bottom set of data and line in the Figure). The data show that 1,25-dihydroxyvitamin D₂ has a similar effect on IAP compared to 19-nor, 1,25-dihydroxyvitamin $D_2$ and another vitamin D analog.

The foregoing description is given for clearness of understanding only, and no unnecessary limitations should be understood therefrom, as modifications within the scope of the invention may be apparent to those having ordinary skill in the art.

All patents, publications and references cited herein are hereby fully incorporated by reference. In case of conflict between the present disclosure and incorporated patents, publications and references, the present disclosure should control.

Throughout the specification, where compositions are described as including components or materials, it is contemplated that the compositions can also consist essentially of, or consist of any combination of the recited components or materials, unless described otherwise.

The practice of a method disclosed herein, and individual steps thereof, can be performed manually and/or with the aid of mechanical and/or electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, it will be recognized that some of the individual steps may be combined, omitted, or further subdivided into additional steps.

What is claimed is:

1. A method for safely lowering or maintaining lowered serum intact parathyroid hormone in a human patient, comprising administering to the patient an effective amount of 1,25-dihydroxyvitamin $D_2$ to lower or maintain lowered serum parathyroid hormone levels without causing substantially increased risk of hypercalcemia or hyperphosphatemia.

2. The method of claim 1, further comprising concurrently
   (a) increasing or maintaining serum calcium levels in the patient;
   (b) maintaining serum phosphorous levels in the patient; and
   (c) increasing or maintaining serum 1,25-dihydroxyvitamin D levels in the patient by said administration of 1,25-dihydroxyvitamin $D_2$.

3. The method according to claim 2, comprising increasing or maintaining serum calcium levels in the patient in a range of about 8.6 to 10.2 mg/dL by said administration of 1,25-dihydroxyvitamin $D_2$.

4. The method according to claim 2, comprising maintaining phosphorous levels in the patient in a range of 2.5 to 4.5 mg/dL by said administration of 1,25-dihydroxyvitamin $D_2$.

5. The method according to claim 2, comprising increasing serum 1,25-dihydroxyvitamin D levels in the patient to the patient's normal historical physiological range by said administration of 1,25-dihydroxyvitamin $D_2$.

6. The method according to claim 2, comprising maintaining serum 1,25-dihydroxyvitamin D levels in the patient's normal historical physiological range for at least 30 days by said administration of 1,25-dihydroxyvitamin $D_2$.

7. The method according to claim 1, wherein said effective amount is sufficient to lower serum intact parathyroid hormone levels by at least 15%.

8. A method of safely increasing or maintaining blood concentrations of 1,25-dihydroxyvitamin D and maintaining serum calcium and phosphorous levels in a human patient with Chronic Kidney Disease by administering an amount of 1,25-dihydroxyvitamin $D_2$ to the patient.

9. A method of alleviating one or more symptoms of 1,25-dihydroxyvitamin D deficiency in a human patient with Chronic Kidney Disease, comprising administering an amount of 1,25-dihydroxyvitamin $D_2$ to the patient such that one or more symptoms of 1,25-dihydroxyvitamin D deficiency are alleviated and serum calcium and phosphorous levels are maintained.

10. The method of claim 9, wherein said one or more symptoms of 1,25-dihydroxyvitamin D deficiency comprise symptoms of deficiency in the non-classical effects of vitamin D.

11. The method of claim 10, wherein said administration of 1,25-dihydroxyvitamin $D_2$ to the patient provides negative endocrine regulation of the renin-angiotensin system in the patient.

12. The method according to claim 1, wherein the patient has been diagnosed with chronic kidney disease (CKD).

13. The method according to claim 12, wherein the patient has been diagnosed with hyperparathyroidism secondary to chronic kidney disease (SHPT).

14. The method according to claim 12, wherein said CKD is Stage 1 or Stage 2 CKD.

15. The method according to claim 12, wherein said CKD is Stage 3, Stage 4, or Stage 5 CKD.

16. The method according to claim 15, wherein the amount of amount of 1,25-dihydroxyvitamin $D_2$ administered is sufficient to reduce serum levels of PTH to 35-70 pg/mL for a Stage 3 CKD patient, to 70-110 pg/mL for a Stage 4 CKD patient, and to 150-300 pg/mL for a Stage 5 CKD patient.

17. The method according to claim 1, wherein the amount 1,25-dihydroxyvitamin $D_2$ administered is in a range of 0.1 µg per week to about 100 µg per week.

18. The method according to claim 1, comprising administering 1,25-dihydroxyvitamin $D_2$ for at least 30 days.

19. The method according to claim 18, comprising administering 1,25-dihydroxyvitamin $D_2$ for at least 2 months.

20. The method according to claim 18, comprising administering 1,25-dihydroxyvitamin $D_2$ for at least 6 months.

21. The method according to claim 18, further comprising avoiding progressive loss of 25-hydroxyvitamin D and 1,25-dihydroxyvitamin $D_3$ in the patient.

* * * * *